US 10,667,743 B2

(12) United States Patent
Yoon et al.

(10) Patent No.: US 10,667,743 B2
(45) Date of Patent: Jun. 2, 2020

(54) DEVICE AND METHOD OF UNCONSCIOUS NOCTURNAL PENILE TUMESCENCE DIAGNOSIS BASED ON NEAR FIELD COMMUNICATION AND PROGRESSIVE SENSING

(71) Applicants: Seoul National University R&DB Foundation, Seoul (KR); Korea University Research and Business Foundation, Seoul (KR)

(72) Inventors: Sung Roh Yoon, Seoul (KR); Jae Young Park, Seoul (KR); Sung Woon Choi, Gyeonggi-do (KR)

(73) Assignees: Seoul National University R&DB Foundation, Seoul (KR); Korea University Research & Business Foundation, Seoul (KR)

( * ) Notice: Subject to any disclaimer, the term of this patent is extended or adjusted under 35 U.S.C. 154(b) by 39 days.

(21) Appl. No.: 15/934,169

(22) Filed: Mar. 23, 2018

(65) Prior Publication Data
US 2018/0206777 A1 Jul. 26, 2018

Related U.S. Application Data

(63) Continuation of application No. PCT/KR2016/010690, filed on Sep. 23, 2016.

(30) Foreign Application Priority Data

Sep. 23, 2015 (KR) .................. 10-2015-0134969
Sep. 23, 2015 (KR) .................. 10-2015-0134972
Sep. 23, 2015 (KR) .................. 10-2015-0134980

(51) Int. Cl.
*A61B 5/00* (2006.01)
*G16H 50/20* (2018.01)
(Continued)

(52) U.S. Cl.
CPC .......... *A61B 5/4393* (2013.01); *A61H 19/00* (2013.01); *G06F 19/00* (2013.01); *G16H 40/63* (2018.01);
(Continued)

(58) Field of Classification Search
CPC ..... A61B 5/4393; A61B 5/004; A61B 5/0004; A61B 5/1075; A61B 5/4806; A61B 5/742;
(Continued)

(56) References Cited

U.S. PATENT DOCUMENTS 4,169,463 A * 10/1979 Piquard ............... A61B 5/0535
600/506
5,482,039 A 1/1996 Place
(Continued)

FOREIGN PATENT DOCUMENTS

JP 1994-133951 A 5/1994
JP 2012-509135 A 4/2012
(Continued)

*Primary Examiner* — Paula J Stice
(74) *Attorney, Agent, or Firm* — Nelson Mullins Riley & Scarborough LLP; Kongsik Kim, Esq.

(57) ABSTRACT

Disclosed herein are a penile tumescence diagnosis device and method. The penile tumescence diagnosis device includes: a plurality of ring sensors configured to measure a body part of a user and generate sensor-sensed information; and a processor configured to generate diagnostic information about the body part of the user based on the sensor-sensed information generated by the plurality of ring sensors. The plurality of ring sensors includes: a first ring sensor configured to have a first threshold length and be disposed on the body part to surround the body part in a ring shape; and a second ring sensor configured to have a second
(Continued)

threshold length larger than the first threshold length and be disposed on the body part to surround the body part in a ring shape.

13 Claims, 16 Drawing Sheets

(51) Int. Cl.
*G16H 50/30* (2018.01)
*G16H 40/63* (2018.01)
*A61H 19/00* (2006.01)
*G06F 19/00* (2018.01)
*A61B 5/01* (2006.01)
*A61B 5/107* (2006.01)

(52) U.S. Cl.
CPC ............. *G16H 50/20* (2018.01); *G16H 50/30* (2018.01); *A61B 5/0004* (2013.01); *A61B 5/01* (2013.01); *A61B 5/1075* (2013.01); *A61B 5/4806* (2013.01); *A61B 5/742* (2013.01)

(58) Field of Classification Search
CPC ........ A61H 19/00; A61H 50/30; A61H 50/20; A61H 40/63; G06F 19/00
See application file for complete search history.

(56) References Cited

U.S. PATENT DOCUMENTS

| | | | |
|---|---|---|---|
| 6,015,393 A * | 1/2000 | Hovland | ............... A61B 5/4393 346/33 ME |
| 6,162,188 A * | 12/2000 | Barnea | ................. A61B 5/4393 600/587 |
| 7,623,923 B2 | 11/2009 | Gerber et al. | |
| 8,118,750 B2 | 2/2012 | Gerber | |
| 8,628,466 B2 | 1/2014 | Orten et al. | |
| 2010/0016759 A1 | 1/2010 | Lavoisier | |
| 2010/0292615 A1 | 11/2010 | Niederberger | |
| 2011/0160600 A1 | 6/2011 | Wu et al. | |
| 2011/0295156 A1 | 12/2011 | Arturi | |
| 2014/0171767 A1 | 6/2014 | Hotaling | |
| 2014/0336452 A1 | 11/2014 | Shahoian et al. | |

FOREIGN PATENT DOCUMENTS

| | | |
|---|---|---|
| KR | 10-2002-0082869 A | 10/2002 |
| KR | 10-0355816 B1 | 10/2002 |
| KR | 10-2011-0030443 A | 3/2011 |
| KR | 10-2013-0012606 A | 2/2013 |

* cited by examiner

DEVICE AND METHOD OF UNCONSCIOUS NOCTURNAL PENILE TUMESCENCE DIAGNOSIS BASED ON NEAR FIELD COMMUNICATION AND PROGRESSIVE SENSING

CROSS-REFERENCE TO RELATED APPLICATION

This application is a continuation of PCT/KR2016/010690 filed on Sep. 23, 2016, which claims priority to Korean Patent Application Nos. 10-2015-0134969, 10-2015-0134972, and 10-2015-0134980 filed on Sep. 23, 2015, which applications are incorporated herein by reference.

TECHNICAL FIELD

The present invention relates to a short-range communication and progressive sensing-based unconscious nocturnal penile tumescence diagnosis device and method and, more particularly, to a penile tumescence diagnosis device and method which use short-range communication and progressive sensing in order to prevent a user's sleep from being disturbed.

BACKGROUND ART

Determining whether the cause of erectile dysfunction is a psychogenic problem originating from a mental problem or an organic problem originating from a physical problem is helpful in the general treatment of erectile dysfunction. The most useful method for diagnosing the cause of erectile dysfunction is a nocturnal (sleep) penile tumescence measurement method using a commercialized computer erection analyzer (for example, RigiScan® Plus). Men normally have three to five erections during sleep. The clinical value of this phenomenon is that the phenomenon is a desirable indicator for distinguishing between erectile dysfunction and a normal state.

For example, when erections of a penis occur during sleep, this case may be judged as being normal. In contrast, when the state of an erection of the penis is weak or an erection of the penis does not occur, this case may be judged as being involved with erectile dysfunction. Accordingly, nocturnal penile tumescence measurement during sleep is an important part of erectile dysfunction treatment.

Furthermore, to achieve a satisfactory sexual activity, it is important to have sufficient penile rigidity and erectile duration during the erection of a penis. When a penis does not become rigid or becomes soft immediately after being rigid, a sexual activity cannot be maintained.

A conventional computer erection analyzer measures nocturnal penile tumescence by hanging rings on the head and bottom of a penis. However, the conventional computer erection analyzer is bulky, and may thus disturb the sleep of a subject.

An example of the solution to the problem in which nocturnal penile tumescence measurement disturbs the sleep of a subject is disclosed in Korean Patent Application Publication No. 10-2011-0030443 entitled "Apparatus and Method for Measuring and Treating Penile Rigidity and Erection and Arterial/Venous Flow."

In order to measure penile rigidity and erection and arterial/venous flow during sleep, this conventional technology includes: placing a sensor 2 or 50 configured to have a means for detecting pressure ICP in the cavernous body of a penis P and a change in the pressure and at least one converter 21 or 55 integrated with the sensor 2 or 50 or offset from the sensor and configured to convert a pressure signal, output from the pressure detection means, into an electric signal around the penis P; and connecting the sensor 2 or 50 to a housing 35, including a means for amplifying and recording a signal output from the transducer 21 or 55, and a means for analyzing the signal by means of a microprocessor in order to measure the fatigue state of an ischiocavernous muscle (IC) and to measure a change in the force of the ischiocavernous muscle (IC) and a change in arterial/venous flow in the cavernous body.

However, this conventional technology is problematic in that it is burdensome to connect the test apparatus to a computer and then analyze data because the test apparatus collects data offline, and is also problematic in that the apparatus is expensive. Furthermore, this conventional technology is problematic in that data obtained via hard measurement may be lost during movement. Accordingly, a more efficient method is required.

Another example of the solution to the problem in which nocturnal penile tumescence measurement disturbs the sleep of a subject is disclosed in Japanese Unexamined Patent Application Publication No. 1944-133951 entitled "NPT Test Apparatus."

The second conventional technology is configured such that a gallium-indium alloy maintained in a liquid phase at room temperature to thus have conductivity or electric resistance is encapsulated in an elastic tube, a pair of external connection conductors configured to form a sensor loop and thus have electrode terminals in contact with the encapsulated alloy at both ends are mounted, and a measuring circuit configured to measure an electric resistance value between both ends of the tube is included.

However, the second conventional technology is problematic in that the gallium-indium alloy having an electric resistance value between both ends of the tube is expensive and in that a motor is used to measure the circumference and rigidity of a body part of a user, and thus battery consumption and noise occur due to the operation of the motor.

Still another example of the solution to the problem in which nocturnal penile tumescence measurement disturbs the sleep of a subject is disclosed in U.S. Patent Application Publication No. 2011/0288370 entitled "Method and Means for Erection Enhancement."

The third conventional technology includes a method and means for enhancing the function of a body part of a user by using a small-sized motor (vibrator) in order to improve the erectile state of the body part of the user.

However, the third conventional technology is also problematic in that it is impossible to control vibration to suit a body part of a user while taking into account the strength, operation time and operation intervals of the motor (vibrator) in response to a change in the body part of the user.

SUMMARY OF THE DISCLOSURE

Men normally have 3 to 5 erections during sleep. The clinical value of this phenomenon is that the phenomenon is a desirable indicator for distinguishing between erectile dysfunction and a normal state. However, computer test equipment is problematic in that it is bulky and expensive. The diagnosis of erectile dysfunction during sleep can be used as a reference for the diagnosis of other diseases. In this case, related prevalence may be more than 50% depending on disease. In particular, the correlation between cardiovascular disease and erectile dysfunction is high. Although it is not easy to constantly monitor cardiovascular disease, the diagnosis of erectile dysfunction can be made in an unconscious state during sleep by using the present invention, thereby enabling remote diagnosis and in-home diagnosis. Therefore, the present invention can provide a measure which enables the risk of cardiovascular disease to be relatively easily monitored in a home environment.

An object of the present invention is to propose a diagnosis device which can be fabricated in small size and light weight and implemented at low cost through the improvement of a diagnosis device which measures the nocturnal penile tumescence of a subject (user) during sleep. An object of the present invention is to propose a method for transferring sensor-sensed information detected by a sensor to a communication device by means of the sensor and the communication device via short-range communication, thereby making the diagnosis device small and lightweight and also improving the economic efficiency of the diagnosis device.

An object of the present invention is to propose a method of generating diagnostic information regarding a body part of a user by means of a processor by using a sensing signal detected by a ring-shaped sensor, thereby making the diagnosis device small and lightweight and also improving the economic efficiency of the diagnosis device.

Furthermore, an object of the present invention is to propose a penile tumescence diagnosis device which can be fabricated in small size and light weight and implemented at low cost through the addition of a vibration module to a diagnosis device which measures the nocturnal penile tumescence of a subject (user) during sleep. The present invention proposes a method of controlling a change in a body part of the user through the addition of the vibration module and generating diagnostic information regarding the body part of the user by means of a processor by using a sensing signal detected by a sensor, thereby making the diagnosis device small and lightweight and also improving the economic efficiency of the diagnosis device.

Furthermore, another object of the present invention is to propose a method which enables a user to take a user to take health examinations while wearing a diagnosis device not only during sleep but also during daily life because the diagnosis device can be fabricated in small size and light weight.

An object of the present invention is to provide a more accurate diagnosis result by storing the personal data of a subject (user), a habit which may influence health, the presence or absence of a disease, a past medical history, and a past diagnosis record in a communication device in advance.

Furthermore, an object of the present invention is to extracts on one or more valid events from a sensing signal detected by a sensor, to make a diagnosis, to visualize the result of the diagnosis and the sensing signal, and to provide the visualized information to a user.

Moreover, an object of the present invention is to, when measuring changes in a body part of a user over time, reduce measuring time and provide a more accurate diagnosis of a psychogenic problem or organic problem by using a vibration module.

According to an aspect of the present invention, there is provided a penile tumescence diagnosis device, including: a plurality of ring sensors configured to measure a body part of a user and generate sensor-sensed information; and a processor configured to generate diagnostic information about the body part of the user based on the sensor-sensed information generated by the plurality of ring sensors.

In this case, the plurality of ring sensors may include: a first ring sensor configured to have a first threshold length and be disposed on the body part to surround the body part in a ring shape; and a second ring sensor configured to have a second threshold length larger than the first threshold length and be disposed on the body part to surround the body part in a ring shape.

The first ring sensor may include a first body formed such that both ends thereof are to be spaced apart from each other, and a first tip sensor pair disposed at the both ends of the first body; and the second ring sensor may include a second body formed such that both ends thereof are to be spaced apart from each other, and a second tip sensor pair disposed at the both ends of the second body.

Each of the first body and the second body may have elasticity, the first tip sensor pair may determine whether the elements of the first tip sensor pair are in contact with each other or spaced apart from each other in response to a change in the body part and generate first state information, and the second tip sensor pair may determine whether elements of the second tip sensor pair are in contact with each other or spaced apart from each other in response to the change in the body part and generates second state information.

The sensor-sensed information generated by the plurality of ring sensors may include the first state information generated by the first tip sensor pair and the second state information generated by the second tip sensor pair.

The processor may be further configured to: derive a first comparison result between the circumference of the body part and the first threshold length and a second comparison result between the circumference of the body part and the second threshold length based on the first state information and the second state information; and sequentially determine a switch in the first state information of the first tip sensor pair and a switch in the second state information of the second tip sensor pair based on the first comparison result and the second comparison result in response to the change in the body part.

The processor may be further configured to: determine whether the sequence of the switch in the first state information and the switch in the second state information matches a predetermined sequence; and determine whether the sensor-sensed information of the sensors is valid based on whether the sequence of the switch in the first state information and the switch in the second state information matches the predetermined sequence.

The penile tumescence diagnosis device may further include memory configured to store the sensor-sensed information detected by the plurality of ring sensors based on sensing time, and the processor may be further configured to: include a receiving module configured to receive the sensor-sensed information detected by the plurality of ring sensors; and generate the diagnostic information regarding the body part based on the sensor-sensed information stored in the memory based on the sensing time.

The first body and the second body may be attached to the body part of the user to surround the body part of the user in a ring shape, with the length of each of the first body and the second body adjusted to suit the shape of the body part of the user.

The processor may be further configured to: determine whether the sensor-sensed information corresponds to a valid event based on the duration and peak value of a sensing signal included in the sensor-sensed information; when the sensor-sensed information corresponds to a valid event, generate body information regarding the body part based on the sensor-sensed information; and when the case where the sensor-sensed information does not correspond to a valid event occurs successively, determine whether one or more of the sensors have failed, have caused error, or have been separated from the body part.

The processor may further include a display control module configured to visualize the sensor-sensed information stored in the memory based on the sensing time. In this case, the display control module may be further configured to display both the sensor-sensed information and the health state of the body part based on the sensing time according to information about the user.

The information about the user may include the personal data of the user, a habit which may influence the health of the user, the presence or absence of a disease, a past medical history, a past diagnosis history, and/or the like. When the health state of the body part is additionally displayed based on the sensing time, the health state of the body part may be displayed for each portion where a main event occurs based on the sensor-sensed information, and the determination result of the health state of the body part may be additionally displayed. In this case, examples of the determination result may include information about whether a currently measured event is a valid event, information about whether the determination that a user is healthy can be made based on currently displayed information, and the like.

According to another aspect of the present invention, there is provided a penile tumescence diagnosis method, the penile tumescence diagnosis method being performed by a diagnosis device including a processor, the penile tumescence diagnosis method including: measuring, by a plurality of ring sensors, a body part of a user, and generating, by the plurality of ring sensors, sensor-sensed information; and generating, by the processor, diagnostic information regarding the body part of the user based on the sensor-sensed information.

In this case, the generating, by the plurality of ring sensors, sensor-sensed information may include: generating, by a first tip sensor pair which is disposed at both ends of a first body configured to have a first threshold length and to be disposed on the body part to surround the body part in a ring shape and formed such that the both ends thereof are to be spaced apart from each other, first state information regarding whether the elements of the first tip sensor pair are in contact with each other or are spaced apart from each other in response to a change in the body part; and generating, by a second tip sensor pair which is disposed at both ends of a second body configured to have a second threshold length larger than the first threshold length and to be disposed on the body part to surround the body part in a ring shape and formed such that the both ends thereof are to be spaced apart from each other, second state information regarding whether the elements of the second tip sensor pair are in contact with each other or are spaced apart from each other in response to the change in the body part.

The generating, by the processor, diagnostic information may include: deriving a first comparison result between the circumference of the body part and the first threshold length and a second comparison result between the circumference of the body part and the second threshold length based on the first state information and the second state information; and sequentially determining a switch in the first state information of the first tip sensor pair and a switch in the second state information of the second tip sensor pair based on the first comparison result and the second comparison result in response to the change in the body part.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE DISCLOSURE

Figure 1:
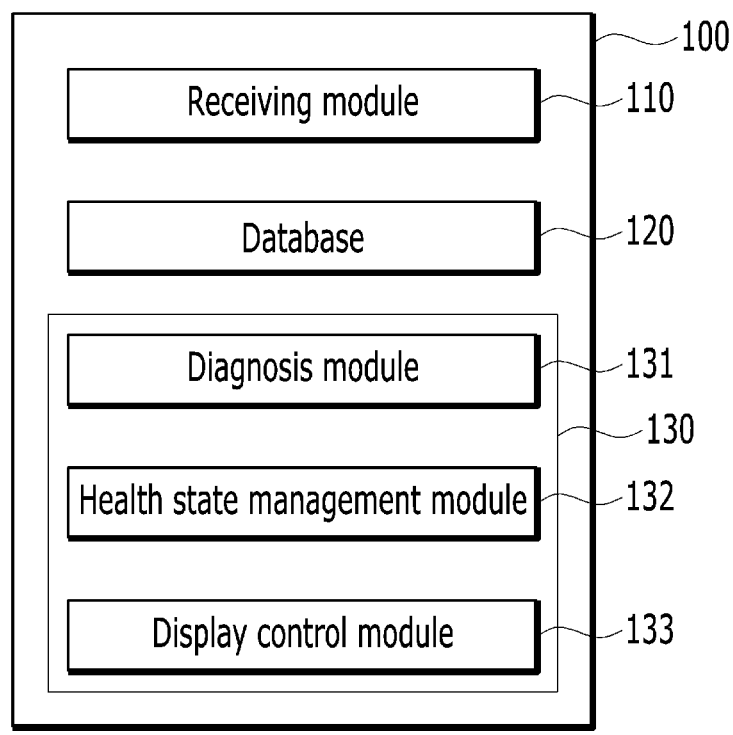
FIG. 1 is a block diagram showing a penile tumescence diagnosis device according to an embodiment of the present invention.

Erectile dysfunction refers to the inability to achieve or maintain a penile erection sufficient for satisfactory sexual performance. Many men suffer from the degradation of the quality of life and stress (see NIH Consensus Conference. Impotence. NIH consensus development panel on impotence. JAMA 1993; 270: 83-90).

Feldman et al. (see Feldman H A, Goldstein I, Hatzichristou D G, Krane R J, McKinlay J B. Impotence and its medical and psychosocial correlates: results of the Massachusetts Male Aging Study. J Urol 1994; 151: 54-61) conducted an epidemiological study on sexual functionality in the general population, identified prevalence and physiological and psychological correlations regarding erectile dysfunction, and presented standard data on erectile dysfunction via the Massachusetts Male Aging Study. According to this study, the prevalence of erectile dysfunction in men aged 40 to 70 years was 52%, and the percentage of erectile dysfunction of intermediate and higher levels was 35%. In Korean studies, 13.4% of the 1,570 patients aged 40 to 79 years were diagnosed with erectile dysfunction via epidemiologic survey, and 32.4% were diagnosed with erectile dysfunction via questionnaire survey (see Ahn T Y, Park J K, Lee S W, Hong J H, Park N C, Kim J J, et al. Prevalence and risk factors for erectile dysfunction in Korean men: results of an epidemiological study. J Sex Med 2007; 4: 1269-76). More than 80% of these causes of erectile dysfunction were organic causes, and many of them were vascular erectile dysfunction (see Quam J P, King B F, James E M, Lewis R W, Brakke D M, Ilstrup D M, et al. Duplex and color Doppler sonographic evaluation of vasculogenic impotence. AJR Am J Roentgenol 1989; 153: 1141-7). This is caused by a decrease in the arterial blood flow into the corpus cavernosum or by a failure in filling the corpus cavernosum with blood due to the obstruction of the vein occlusion function (see Sattar A A, Wery D, Golzarian J, Raviv G, Schulman C C, Wespes E. Correlation of nocturnal penile tumescence monitoring duplex ultrasonography and infusion cavernosometry for the diagnosis of erectile dysfunction. J Urol 1996; 155: 1274-6). Furthermore, it was reported that the majority of those patients had at least one risk factor for cardiovascular disease, such as hypertension, diabetes, hyperlipidemia, smoking, obesity, etc. (see Feldman H A, Goldstein I, Hatzichristou D G, Krane R J, McKinlay J B. Impotence and its medical and psychosocial correlates: results of the Massachusetts Male Aging Study. J Urol 1994; 151: 54-61, Feldman H A, Johannes C B, Derby C A, Kleinman K P, Mohr B A, Araujo A B, et al. Erectile dysfunction and coronary risk factors: prospective results from the Massachusetts male aging study. Prev Med 2000; 30: 328-38, Bortolotti A, Parazzini F, Colli E, Landoni M. The epidemiology of erectile dysfunction and its risk factors. Int J Androl 1997; 20: 323-34, Roumeguere T, Wespes E, Carpentier Y, Hoffmann P, Schulman C C. Erectile dysfunction is associated with a high prevalence of hyperlipidemia and coronary heart disease risk. EurUrol 2003; 44: 355-90) and that the prevalence of erectile dysfunction was higher in patients with cardiovascular disease than the general population (see Kloner R A. Erectile dysfunction in the cardiac patient. CurrUrol Rep 2003; 4: 466-71, Kim H W, Park W J, Cho S Y. Erectile dysfunction in the patients with cardiovascular disease. Korean J Urol 2006; 47: 279-86). Accordingly, there is a growing interest in the correlations between cardiovascular disease and vascular erectile dysfunction. In the cohort study conducted on a population of 2,519 persons in Korea, lifestyle habits, such as drinking, an exercise habit, and smoking cessation, were not correlated with the risk of erectile dysfunction, but risk factors for cardiovascular disease, such as hypertension, hypercholesterolemia greater than 240 mg/dl, and smoking, were correlated with erectile dysfunction (see Yang D H, Jeong J Y, Jang S N, Lee S K, Choi Y J, Kim D H. Prevalence and risk factors for erectile dysfunction in aging men: Hallym Aging Study HAS. Korean J Urol 2007; 48: 1258-76). In particular, erectile dysfunction was thought to be a precursor symptom observed before the onset of cardiovascular disease, and it was reported that in the erectile dysfunction group, the functions of the vascular endothelium and the left ventricle were lowered compared to the control group (see Uslu N, Eren M, Gorgulu S, Alper A T, Orhan A L, Yildirim A, et al. Left ventricular diastolic function and endothelial function in patients with erectile dysfunction. Am J Cardiol 2006; 97: 1785-8). Coronary artery disease is caused by endothelial dysfunction, an obstructive vascular change, or the like, and has a great influence on the vascular system of the corpus cavernosum. That is, a decrease in the velocity of blood flow and a decrease in the compliance of the blood vessel attributable to a reduction in the inner diameter of the blood vessel may lead to a reduction in the blood pressure systolic blood flow, and a decrease in the corpus cavernosus blood flow may cause a decrease in corpuscular pressure, thus resulting in venous occlusive erectile dysfunction (see Kim H W, Park W J, Choi Y S, Cho S Y. The correlation between erectile dysfunction and the severity of coronary artery involvement in patients with coronary artery disease. Korean J Urol 2007; 48: 94-102). Diabetes is also highly correlated with erectile dysfunction. It has been reported that generally, 20 to 85% of diabetes patients have erectile dysfunction (see Son H, Byun S S, Park E, Cho K S, Jo M K, Kim S W, et al. Prevalence of sexual dysfunction in men older than 40 living in Seoul: epidemiologic survey using questionnaire. Korean J Uro12002; 43: 52-61, Bancroft J, Gutierrez P. Erectile dysfunction in men with and without diabetes mellitus: a comparative study. Diabet Med 1996; 13: 84-920). Klein et al. reported that, as the duration of diabetes became longer and the control of blood glucose became poorer, erectile dysfunction increased (see Klein R, Klein B E, Lee K E, Moss S E, Cruickshanks K J. Prevalence of self-reported erectile dysfunction in people with long-term IDDM). Diabetes Care 1996; 19: 135-41). In the case of diabetic patients, erectile dysfunction is caused by a blood vessel change and neural damage attributable to arteriosclerosis. Benvenuti et al. reported that vascular occlusion rather than neural damage was the cause of erectile dysfunction in the case of diabetic patients (see Benvenuti F, Boncinelli L, Vignoli G C. Male sexual impotence in diabetes mellitus: vasculogenic versus neurogenic factors. Neurourol Urodyn 1993; 12: 145-51). As can be seen from the results of various studies, erectile dysfunction may be viewed as not only a functional problem in which the penises of men cannot be erected but also a barometer of the health of men closely correlated with major chronic diseases.

As described above, the diagnosis of erectile dysfunction during sleep can be used as a reference for the diagnosis of other diseases. In this case, related prevalence may be more than 50% depending on disease. In particular, the correlation between cardiovascular disease and erectile dysfunction is high. Although it is not easy to constantly monitor cardiovascular disease, the diagnosis of erectile dysfunction can be made in an unconscious state during sleep by using the present invention, thereby enabling remote diagnosis and in-home diagnosis. Therefore, the present invention can provide a measure which enables the risk of cardiovascular disease to be relatively easily monitored in a home environment.

Other objects and features of the present invention besides the above objects will be apparent by reference to the following description of embodiments taken with reference to the accompanying drawings.

Embodiments of the present invention will be described in detail with reference to the accompanying drawings. In the following description of the present invention, when it is determined that a detailed description of a related well-known component or function may make the gist of the present invention obscure, the detailed description will be omitted.

The prevent invention is not limited by or to the embodiments. Throughout the accompanying drawings, the same reference symbols designate the same components. An overall system in which a penile tumescence diagnosis function is performed will be described with reference to FIG. 8 first, and then detailed descriptions will be given with a focus on the characteristic configurations of the present invention.

Figure 8:
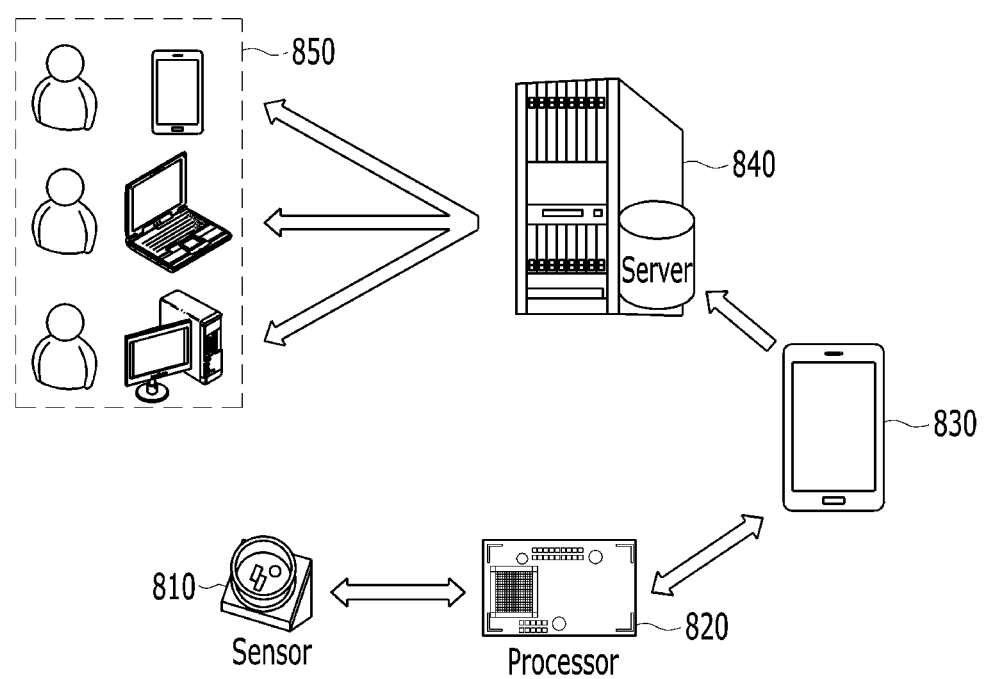
FIG. 8 is a view showing a penile tumescence diagnosis system according to an embodiment of the present invention.

FIG. 8 is a view showing a penile tumescence diagnosis system according to an embodiment of the present invention.

The penile tumescence diagnosis system may measure information about a specific body part of a user (subject), may diagnose the state of the body part based on the measured information about the body part, may store/manage diagnostic information over a communication network, and may share or use the diagnostic information for the public benefit when necessary. It will be apparent that to share or use the diagnostic information, it is necessary to perform processing work to exclude personal information therefrom. Meanwhile, the diagnostic information may be provided to the user (subject) such that it can be used only for the user's (subject's) own personal purposes.

The penile tumescence diagnosis system includes a sensor 810, a processor 820, a communication device 830, and a server 840.

The sensor 810 directly comes into contact with a specific body part of a user, detects changes in the body part over time, and generates a sensing signal or sensor-sensed information. In an embodiment, the sensor 810 may include an analog-digital converter configured to digitize the sensing signal measured in an analog domain, and may also include memory configured to store the sensor-sensed information for a predetermined number of time frames. In another embodiment, the sensor 810 may transmit the measured sensing signal directly to the processor 820 in real time.

The processor 820 may receive the sensing signal or sensor-sensed information from the sensor 810, and may diagnose the state of the specific body part based on the sensing signal or sensor-sensed information. The processor 820 may generate primary diagnostic information regarding a first health state of the specific body part, and may transmit the primary diagnostic information to the communication device 830 and the server 840 so that it can be shared/managed as desired.

An example of the body part of the user may be a man's penis. In this case, the sensor 810 may detect raw data on the rigidity of the penis, the circumferential length of the penis, a temperature on the skin of the penis, a temperature attributable to blood flow inside the penis, and/or the like, or data obtained by processing/correcting raw data, as a sensing signal or sensor-sensed information.

The processor 820 may be connected to the sensor 810 via wired communication, or may receive sensor-sensed information via wireless communication. When the sensor 810 and the processor 820 are connected to each other via wired communication, the sensor 810 may transfer the sensing signal directly to the processor 820 without manipulating or processing the sensing signal. In this case, the processor 820 may diagnose the state of the specific body part based on the sensing signal, and may perform a function identical to that of a diagnosis relay device. The diagnostic information generated by the processor 820 may be primary diagnostic information having clinical significance regarding the health state of the specific part. For example, the primary diagnostic information may be information having clinical significance regarding a first health state, such as the erectile sustainability of the penis, the rigidity of the penis, and/or the like.

When the sensor 810 transfers information to the processor 820 via wireless communication, the transfer of the information communication may be limited by the available resources of the wireless communication or may be influenced by a surrounding wireless communication environment. Accordingly, the sensor 810 may convert the detected sensing signal into sensor-sensed information, and may then transfer sensor-sensed information over a predetermined number of time frames to the processor 820 periodically or upon the occurrence of a specific event.

The processor 820 may detect one or more valid events from the sensor-sensed information received from the sensor 810, and may diagnose the first health state of the body part based on the pattern of the sensor-sensed information corresponding to the detected valid events.

In this case, each of the valid events refers to a physiological response which occurs in a user. When a specific physiological response occurs at a measureable level in a signal detected by the sensor 810 and exceeds a measurement threshold value, the physiological response may be considered to be a valid event. The measurement threshold value may include criteria for the magnitude level of a detected signal and the duration of the detected signal. Furthermore, in an embodiment, until a unit event has occurred a predetermined or larger number of times and at a predetermined or higher magnitude level, it is not determined that a valid event has occurred.

The valid event is detected based on the pattern of the sensor-sensed information, i.e., the width of a pulse (erectile duration) and a peak value (the circumferential length of the penis). The processor 820 may diagnose the health state of the specific body part of the user based on the erectile duration and circumferential length of the penis of a typical adult man by detecting the valid events based on the sensing signal of the sensor 810.

The sensor 810 and processor 820 of the present invention may adopt only one or more valid events by eliminating unintended noise or noise attributable to an external shock from the sensing signal. For example, one or more valid events may be extracted by determining a case, such as the case where during the operation of the sensor 810, a user (subject) touches the sensor 810 with his or her hand or the case where a physical shock is applied to the body part where the sensor 810 is installed by the movement of the body, from a sensing signal and then eliminating the unintended phenomenon from the sensing signal. Such an unintended shock or noise may be determined based on the waveform of a sensing signal, the duration in the case where a sensing signal occurs in pulse form, whether a sensing signal increases or decreases sequentially, and/or the like.

The processor 820 transfers the diagnostic information and the sensor-sensed information, received from the sensor 810, to the communication device 830 over a common communication network including a wired communication network and/or a wireless communication network. For example, the transfer may be performed via well-known communication technology, such as TCP/IP, Wi-Fi, Bluetooth, RFID, and/or the like. The communication device 830 may any one of a personal digital assistant (PDA), a mobile phone, a smartphone, a laptop, and the like. The communication device 830 may function as a hub of sensor-sensed information which stores diagnostic information and sensor-sensed information and transmits diagnostic information and sensor-sensed information to the server 840. The diagnostic information and the sensor-sensed information received from the processor 820 are stored in the memory (not shown) of the communication device 830 or a database (not shown) along with sensing time information.

Although the communication between the sensor 810 and the processor 820 and the communication between the processor 820 and the communication device 830 may be performed via wired communication, they may be performed using short-range communication technology, such as Wi-Fi, Bluetooth, RFID, or the like. In particular, a diagnosis device to which only the sensor 810 is coupled or only the sensor 810 and the processor 820 are coupled may significantly improve the convenience of the diagnosis of a user when being installed on a specific body part of the user. Since a user stays in a sleep state with the sensor attached to his or her body for a long time, an appropriate trade-off between the convenience of movement and the precision of a diagnosis is required.

The communication device 830 may transfer the first health state of the specific body part of the user to the server 840. The server 840 may generate secondary diagnostic information based on the primary diagnostic information received via the communication device 830. The server 840 may generate the secondary diagnostic information regarding the second health state of the user by using the primary diagnostic information and information about the user. The information about the user includes all contextual information which needs to be additionally taken into account when the specific body part of the user is diagnosed. For example, the information about the user refers to information including the personal data of the user, a habit (drinking, or smoking) which may influence the health of the user, the presence or absence of a disease, a past medical history, a past diagnosis record, whether a medicine is being administered or not, and/or the like.

For example, the communication device 830 may derive primary diagnostic information regarding the health state of the body part of the user and the overall health state of the user based on the signal of the sensor 810 regarding the body part of the current user by analyzing time-series diagnostic information stored in a database within the communication device 830. The server 840 may additionally derive a decision on a user health state-based future treatment plan based on the primary diagnostic information and the past medical history, diagnosis record, presence or absence of the administration of a medicine, personal data, and/or the like of the user.

Furthermore, the server 840 may generate secondary diagnostic information by collect the primary diagnostic information and then analyzing the primary diagnostic information by means of a time frame based on a scale different from that of the time frame managed within the communication device 830. For example, when the primary diagnostic information is information generated over a time frame of a single day or week, the secondary diagnostic information may information about changes in the health state of the user via primary diagnostic information accumulated over a long period equal to or longer than one month. When the health state information of the user derived as a primary diagnosis result by the communication device 830 is integrated with the information over a longer time frame analyzed by the server 840, there may be derived secondary diagnostic information regarding the tendency of the health state of the user, the determination of whether to administer a medicine to the user for a long period, the change of a treatment method for the user, the determination of a treatment effect, the prognosis of the disease of a patient, and/or the like.

The communication device 830 may receive the secondary diagnostic information generated by the server 840 when necessary. The communication device 830 may receive information about the user, stored in the server 840, from the server 840 within an allowable range. The communication device 830 may provide the information about the user within the allowable range, together with the primary diagnostic information, to the user via the user interface UI of the communication device 830. Furthermore, the communication device 830 may provide a user menu configured to allow at least part of the information about the user to be corrected or checked via the user interface. In this case, the user interface may include a display, a touch screen, a microphone, and a speaker, and refers to an interface capable of providing and receiving information in visual, auditory, and tactile manners.

The communication device 830 may additionally display the result of the determination of whether an occurred main event is a valid event or noise, obtained by the processor 820, for each portion of the sensor-sensed information in which the main event (the portion in which it may be determined that an erection of the penis has occurred) has occurred. When the number of valid events within the time frame satisfies a predetermined reference value, the communication device 830 may additionally display a comment indicating that the user is healthy.

The server 840 may store the primary diagnostic information regarding the first health state of the specific body part of the user or secondary diagnostic information regarding the second health state, and may provide the stored primary or secondary diagnostic information in response to a request from another user or a doctor 850. In this case, it is necessary to perform processing in order to exclude personal information from the information to be provided, as described above.

Although the embodiment in which the processor 820 and the communication device 830 are divided into separate entities is shown in FIG. 8, there may be implemented an embodiment in which the processor 820 is included in the communication device 830. If the communication device 830 is a smartphone, the diagnosis function of the processor 820 may be executed via an application program of the smartphone. FIG. 1 shows a penile tumescence diagnosis device in which the processor 820 and communication device 830 of FIG. 8 have been integrated with each other. Meanwhile, the sensor 810 of FIG. 8 may be one of the progressive sensors which are embodied in FIGS. 9 to 11.

FIG. 1 is a block diagram showing a penile tumescence diagnosis device 100 according to an embodiment of the present invention.

The penile tumescence diagnosis device 100 includes a receiving module 110, a database 120, and a processor 130. The processor 130 includes a diagnosis module 131, a health state management module 132, and a display control module 133.

The penile tumescence diagnosis device 100 may receive sensor-sensed information or a sensing signal from a sensor having measured information about a specific body part of a user (subject), and may diagnose the state of the specific body part based on the received information or signal. The penile tumescence diagnosis device 100 may primarily diagnoses the health state of the body part by using the sensor-sensed information of the sensor, and may transmit the result of the primary diagnosis to another communication device.

The receiving module 110 of the penile tumescence diagnosis device 100 may be connected to the sensor via wired or wireless communication. When the penile tumescence diagnosis device 100 is connected to the sensor via wired communication, the penile tumescence diagnosis device 100 may function as a diagnosis relay device which converts the sensor-sensed information of the sensor into diagnostic information. In this case, the penile tumescence diagnosis device 100 may transmit the diagnostic information to an external communication device or server.

The receiving module 110 of the penile tumescence diagnosis device 100 is attached to the specific body part of the user, and receives sensor-sensed information from the sensor configured to detect changes in the body part over time and to generate sensor-sensed information. The received sensor-sensed information of the user is stored in the database 120 based on sensing time. The processor 130 functions to control the receiving module 110 so that the receiving module 110 can receive the sensor-sensed information of the user over a wired/wireless communication network.

Furthermore, the processor 130 controls the diagnosis module 131 so that the diagnosis module 131 diagnoses the health state of the specific body part of the user by using the sensing time-based sensor-sensed information stored in the database 130. Accordingly, the erectile capability of the user (subject) may be diagnosed by diagnosing the erectile sustainability of the specific body part (penis) of the user (subject) and the rigidity of the penis by using the sensor-sensed information detected by the sensor.

In this case, the diagnosis module 131 may detect one or more valid events from the sensor-sensed information stored in the database 120, and may primarily diagnose the health state of the body part based on the pattern of the sensor-sensed information corresponding to the detected valid events.

The processor 130 may transfer primary diagnostic information regarding the diagnosed first health state of the specific body part of the user to the server, and may control the health state management module 132 so that the health state management module 132 can receive secondary diagnostic information regarding a second health state generated by the server by using information about the user which is related to the diagnosed body part.

The processor 130 may control the display control module 133 so that the display control module 133 can visualize the sensor-sensed information stored in the database based on sensing time.

In this case, the display control module 133 may display both the sensor-sensed information detected by the sensor and the health state of the specific body part of the user diagnosed by the diagnosis module 120, based on sensing time according to information about the user.

Figure 2:
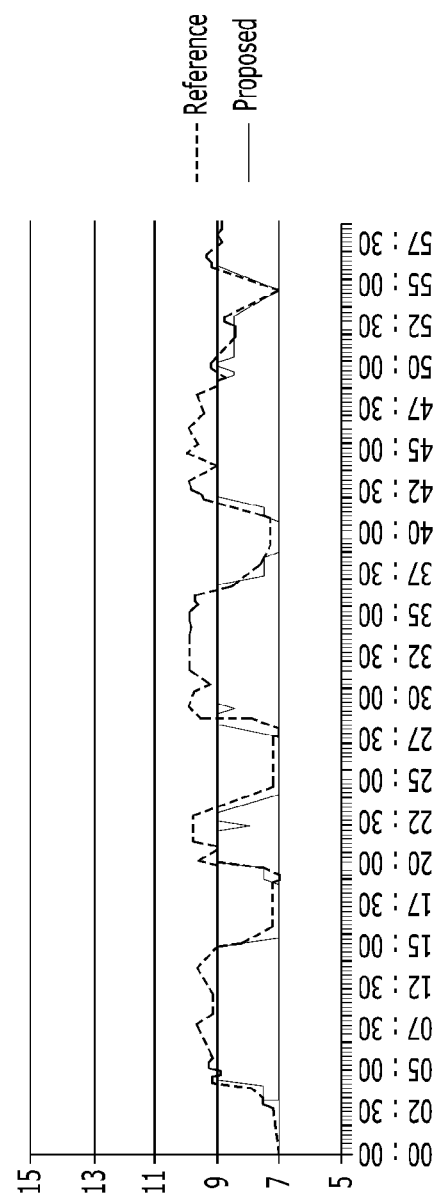
FIG. 2 is a graph showing the comparisons between a diagnosis result over time according to an embodiment of the present invention and a reference diagnosis result.

FIG. 2 is a graph showing the comparisons between a diagnosis result over time according to an embodiment of the present invention and a reference diagnosis result.

Referring to FIG. 2, the sensing signal Proposed detected at intervals of 2 minutes and 30 seconds by the sensor 810 proposed as an embodiment of the present invention is shown. The reference diagnosis result Reference was measured using a widely known RigiScan® product within a time frame which was the same as that of the sensing signal Proposed of the proposed sensor 810. Since the sensing signal of the proposed sensor 810 is detected at digitized levels, a signal above the largest measured value is not identified in an analog domain. However, this is merely an embodiment of the present invention, and the technical spirit of the present invention is not limited thereto.

Since the proposed sensor 810 may generate a measured value of a level sufficient to detect a valid event as a sensing signal as described above, the processor 820 may distinguish a sufficiently valid event from noise by using the sensing signal Proposed. Referring to FIG. 2, it can be seen that the sensing signal Proposed of the proposed sensor 810 and the reference diagnosis result Reference substantially have no difference in terms of the length of the intervals of valid events and the number of valid events.

As described above, the measurement method according to the present invention is advantageous in that the performance thereof is not degraded compared to the conventional diagnosis devices, measurement is enabled using the small, lightweight diagnosis device, and more effective measurement can be performed in an unconscious state during the sleep of a user.

Figure 3:
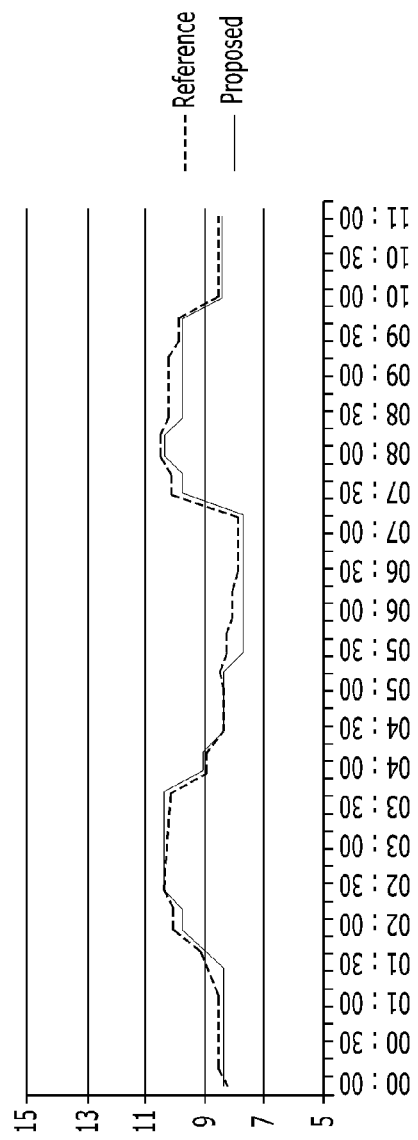
FIG. 3 is a graph showing the comparisons between a diagnosis result over time according to an embodiment of the present invention and a reference diagnosis result.

FIG. 3 is a graph showing the comparisons between a diagnosis result over time according to an embodiment of the present invention and a reference diagnosis result.

Referring to FIG. 3, the sensing signal Proposed detected by the sensor 810 proposed as an embodiment of the present invention at intervals of 30 seconds is shown. The reference diagnosis result Reference was measured using a widely known RigiScan® product within a time frame which was the same as that of the sensing signal Proposed of the proposed sensor 810 in the same manner as shown in FIG. 2.

Since the proposed sensor 810 may generate a measured value of a level sufficient to detect a valid event as a sensing signal as described above, the processor 820 may distinguish a sufficiently valid event from noise by using the sensing signal Proposed. Referring to FIG. 3, it can be seen that the sensing signal Proposed of the proposed sensor 810 and the reference diagnosis result Reference substantially have no difference in terms of the length of the intervals of valid events and the number of valid events.

Figure 4:
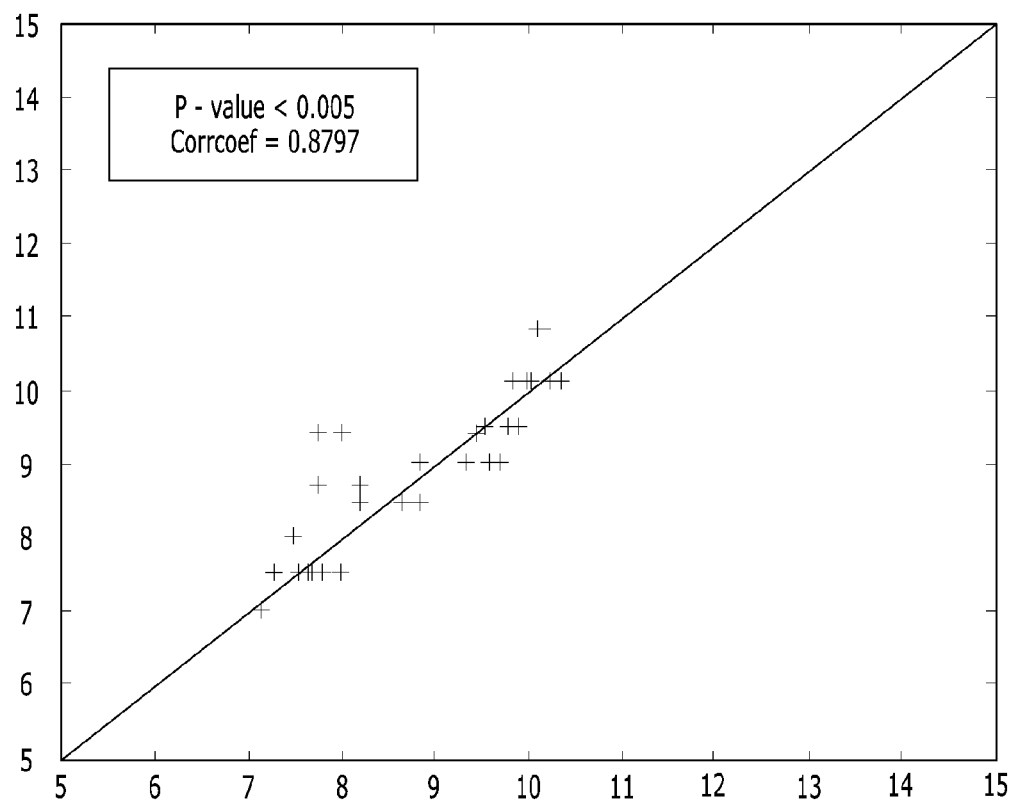
FIG. 4 is a graph showing the correlations between the diagnosis result over time and reference diagnosis result of FIG. 2.

FIG. 4 is a graph showing the correlations between the diagnosis result over time and reference diagnosis result of FIG. 2.

Referring to FIG. 4, the correlations between the sensing signal Proposed of the proposed sensor 810 and the reference diagnosis result Reference are shown by plotting the magnitudes of one or more valid events, occurring in each time span in FIG. 2, on a graph. In other words, the horizontal axis represents the magnitude of the sensing signal Proposed of each valid event, and the vertical axis represents the magnitude of the reference diagnosis result Reference of the valid event. A valid event detected in the same time frame of the sensing signal Proposed and the reference diagnosis result Reference is plotted on the graph of FIG. 4 with the value of the sensing signal Proposed as an x coordinate and the value of the reference diagnosis result Reference as a y coordinate. In other words, on the graph of FIG. 4, each mark + corresponds to one valid event, an x coordinate represents the value of the sensing signal Proposed of a corresponding valid event, and an y coordinate represents the value of the reference diagnosis result Reference of a corresponding valid event.

Referring to FIG. 4, a complete y=x graph indicates that the reference diagnosis result Reference and the sensing signal Proposal completely match each other. However, in practice, a valid event is detected substantially the same number of times, and the detected signal value of each valid event exceeds a reference value of a level sufficient to recognize the validity of an event. Accordingly, the sensing signal Proposal of the proposed sensor 810 may be effectively applied in place of the reference diagnosis result Reference.

Figure 5:
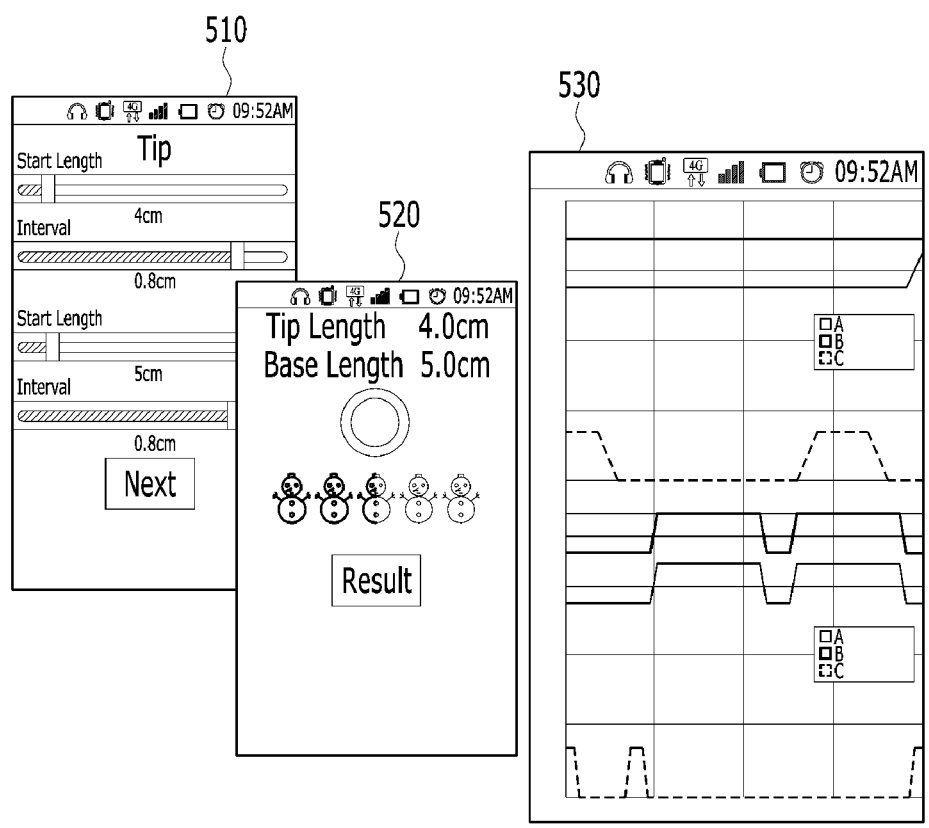
FIG. 5 is a view showing a display screen configured to visualize a penile tumescence sensing signal and then provide the visualized signal to a user according to an embodiment of the present invention.

FIG. 5 is a view showing a display screen configured to visualize a penile tumescence sensing signal and then provide the visualized signal to a user according to an embodiment of the present invention.

FIG. 5 shows an embodiment of the present invention in which the sensor-sensed information and primary diagnostic information stored in the database 120 may be visualized based on sensing time by the display control module 133 in the penile tumescence diagnosis device 100.

The penile tumescence diagnosis device 100 described herein may be a mobile communication device including a smart phone, a PDA, and a mobile phone. Accordingly, the sensor-sensed information and the primary diagnostic information may be displayed together or separately to a user on the screen of the mobile communication device based on the sensing time. In another embodiment of the present invention, the penile tumescence diagnosis device 100 may be a wireless communication-enabled personal computer or another operation processing-enabled electronic device, other than a mobile communication device.

As in a first UI embodiment 510, a user may enter information about the user directly via a user interface UI. As in a second UI embodiment 520, primary diagnostic information regarding the diagnosed health state of a specific body part of a user may be provided to the user.

Furthermore, as in a third UI embodiment 530, both sensor-sensed information (a sensing signal) based on sensing time and information about a user entered by the user may be provided to the user. In this case, the result of the determination of whether an occurred main event is a valid event or noise, obtained by the processor 820, may be additionally displayed for each portion of the sensor-sensed information in which the main event (the portion in which it may be determined that an erection of the penis has occurred) has occurred. When the number of valid events within a time frame satisfies a predetermined reference value, a comment indicating that the user is healthy may be additionally displayed.

Figure 6:
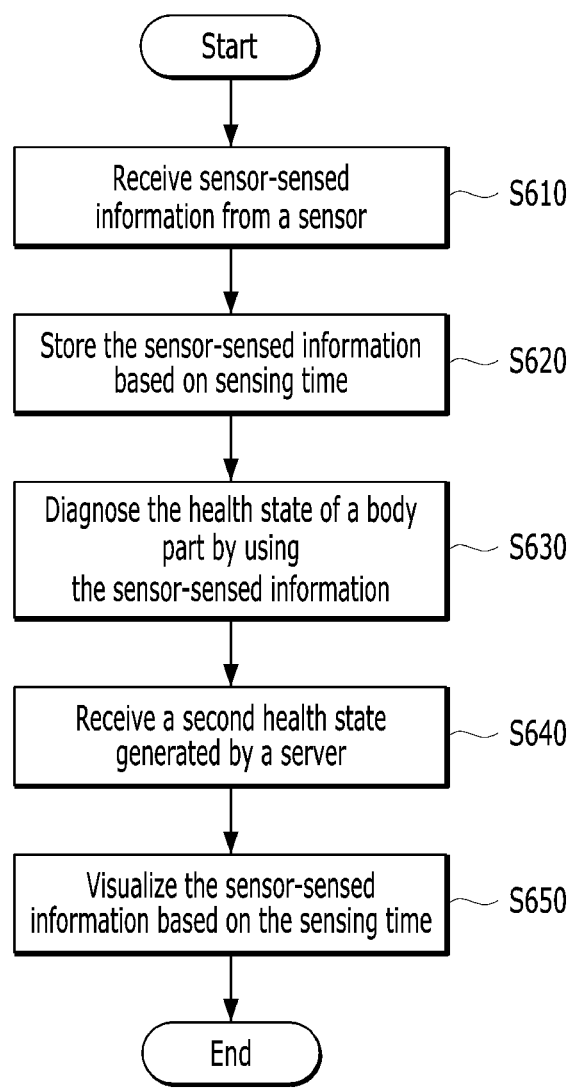
FIG. 6 is an operation flowchart showing a penile tumescence diagnosis method according to an embodiment of the present invention.

FIG. 6 is an operation flowchart showing a penile tumescence diagnosis method according to an embodiment of the present invention.

The penile tumescence diagnosis method according to the embodiment of the present invention configured to measure information about a specific body part of a user (subject) and then transmit the measured information about the body part to a communication device includes step S610 of receiving sensor-sensed information from a sensor configured to be attached to the specific body part of the user and to acquire sensor-sensed information regarding changes in the body part over time. In this case, the body part of the user may be, for example, the penis of the user, in which case time raw data regarding changes in the circumferential length of the penis of the user over time during the sleep of the user may be detected by the sensor, and the sensor-sensed information detected by the sensor may be received.

Furthermore, the sensor-sensed information regarding the user may be received from the sensor over a common communication network including a wired communication network and/or a wireless communication network. The reception of the sensor-sensed information may be performed via well-known communication technology, such as TCP/IP, Wi-Fi, Bluetooth, or the like.

The received sensor-sensed information regarding the user is stored in a database based on sensing time at step S620. The health state of the specific body part of the user is diagnosed using the sensor-sensed information based on sensing time stored in database at step S630. Accordingly, the erectile capability of the user (subject) may be diagnosed by diagnosing the erectile sustainability of the specific body part (penis) of the user (subject) and the rigidity of the penis by using the sensor-sensed information detected by the sensor.

In this case, one or more valid events may be detected from the sensor-sensed information stored in the database, and the health state of the body part may be primarily diagnosed based on the pattern of the sensor-sensed information corresponding to the detected valid events.

Furthermore, the penile tumescence diagnosis method according to the embodiment of the present invention may include step S640 of transferring the diagnosed health state of the specific body part of the user to a server and receiving secondary diagnostic information regarding a second health state generated by the server by using the diagnosed health state of the body part.

In this case, the second health state and the secondary diagnostic information are based on an additional diagnosis made by additionally using information stored in the server. The information about the user includes all contextual information which needs to be additionally taken into account when the specific body part of the user is diagnosed. For example, the information about the user refers to information including the personal data of the user, a habit (drinking, or smoking) which may influence the health of the user, the presence or absence of a disease, a past medical history, a past diagnosis record, whether a medicine is being administered or not, and/or the like, as described above.

The primary diagnostic information refers to direct numerical changes in the size, rigidity, temperature, and/or the like of the specific body part over time. The secondary diagnostic information may include the diagnosis of whether a cause is psychogenic or organic, made by taking into account the primary diagnostic information, general information (age, a disease record, and/or the like) about the user, and additional information, such as the recent stress index of the user, and/or the like, if the primary diagnostic information regarding the user indicates that the user is unhealthy.

In general, organic causes, including aging, smoking, drinking, diabetes, hypertension, cerebrovascular disease, the administration of hormone medicines, part of antihypertensive drugs, or psychotropic drugs, and the surgery or damage of the brain, the spinal cord or the pelvic, are recognized as the causes of erectile dysfunction. Furthermore, chronic diseases, including multiple sclerosis (a chronic neuroimmune system disease occurring in the central nervous system including the brain, the spinal cord, and the optic nerves), other neurological diseases, depression, chronic renal failure and hepatic failure, chronic obstructive pulmonary disease, and skin sclerosis (a disease in which the skin is hardened and loses elasticity), are also mentioned as the causes of erectile dysfunction.

Psychogenic causes, including psychological factors, such as emotional stress, depression, and anxiety disorder without the above-described physical cause, are also mentioned as the causes of erectile dysfunction.

In addition, the daily life habit associated with a disease of the user (subject) may also have influence. In other words, it is widely known that lipid metabolism disorders, such as diabetes, hypertension, obesity, and hypercholesterolemia, and cardiovascular disease caused by smoking and non-exercise habits may act as risk factors for erectile dysfunction.

The penile tumescence diagnosis method according to the embodiment of the present invention may include step S650 of visualizing the sensor-sensed information stored in the database based on the sensing time. In this case, both the sensor-sensed information regarding the user detected by the sensor and the primary diagnostic information may be displayed based on the sensing time according to the information about the user.

Figure 7:
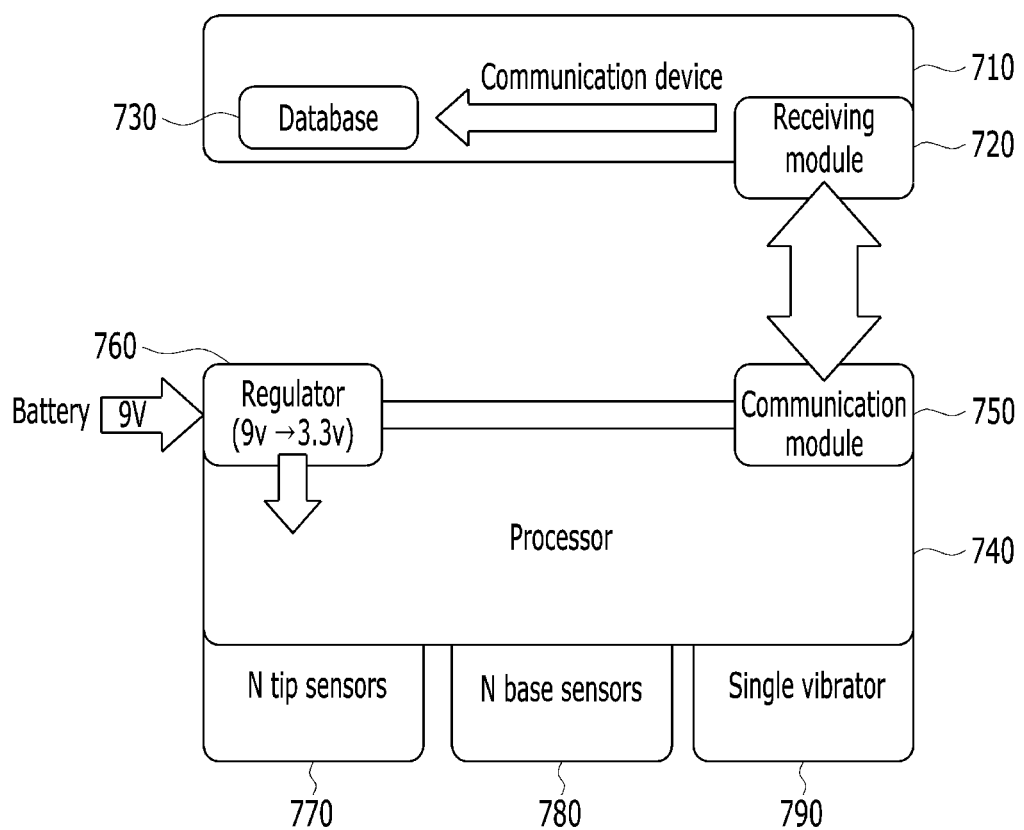
FIG. 7 is a view showing the hardware configuration of a penile tumescence diagnosis device according to an embodiment of the present invention.

FIG. 7 is a view showing the hardware configuration of a penile tumescence diagnosis device according to an embodiment of the present invention.

Referring to FIG. 7, there is shown an embodiment in which sensor units 770 and 780 and a processor 740 are coupled to each other and exchange data with a communication device 710 via a communication module 750.

N tip sensors 770 are installed on the head of a penis and generate sensing signals, and N base sensors 780 are installed on the root of the penis and generate sensing signals. Furthermore, there may be added a single vibrator 790 configured to provide an appropriate stimulus to the penis under the control of the processor 740.

The processor 740 converts the analog domain signals, detected by the sensor units 770 and 780, into sensor-sensed information, and transfers the sensor-sensed information to the communication device 710 via the communication module 750. The driving power of the processor 740 is supplied by a regulator 760. Although an embodiment in which the regulator 760 converts a battery voltage of 9 V into 3.3 V and then supplies the resulting voltage to the processor 740 is shown in FIG. 7, this is only one of the adoptable embodiments, and the technical spirit of the present invention is not limited thereto.

In general, although a battery provides a predetermined voltage of 9 V when fully charged, it provides a voltage lower than the original voltage when electricity has been discharged from the battery due to repeated disoperation, which may be a cause of erroneous operation. Accordingly, the stable operation of the processor 740 may be ensured through the conversion of the voltage of the battery by the regulator 760.

The receiving module 720 of the communication device 710 receives the sensor-sensed information from the communication module 750, and stores the sensor-sensed information, together with sensing time information, in the database 730. The communication device 710 may store and manage the sensor-sensed information by using the sensing time information as an index. Accordingly, the communication device 710 may possess a structural database 730 for the sensor-sensed information, and may thus function as data relay hub.

In an embodiment, the communication device 710 may be a mobile terminal, a PDA, or a laptop. Each of the sensor units 770 and 780 measures the ON/OFF of the n sensors configured to measure the circumference of the body part of a patient in real time, and transmits measured signals to the communication device 710. In order to improve the battery usage efficiency of the sensing hardware, the frequency of communication with the communication device 710 may be adaptively controlled. The damage to a signal resulting from the control of the frequency of communication may be recovered via a recovery algorithm executed in the database 730 of the communication device 710 or via a recovery algorithm executed in the server 840 shown in FIG. 8. The recovery algorithm may be embodied using a channel coding and decoding algorithm for communication.

Referring to FIGS. 7 and 8 together, the communication device 710 of FIG. 7 corresponds to the communication device 830 of FIG. 8. In this case, the diagnosis system according to the present invention may check the daily health state of the patient based on data recovered through the application of the recovery algorithm (the integration of the sensor signal, the maximum length of an erection, etc.), and may issue an alarm to the patient and a medical person when a change in the daily health state is equal to or higher than a predetermined reference value and also the alarm is required. Although the function of checking the daily health state of the patient and determining whether a change in the daily health state is equal to or higher than a predetermined reference value may be performed in the processor of the communication device 710 or 830 or in the server 840, it may be implemented through the cooperation between the processor of the communication device 710 or 830 and the server 840. The communication device 710 or 830 may derive primary diagnostic information having clinical significance, and the server 840 may derive advanced secondary diagnostic information, as described above.

Figure 9:
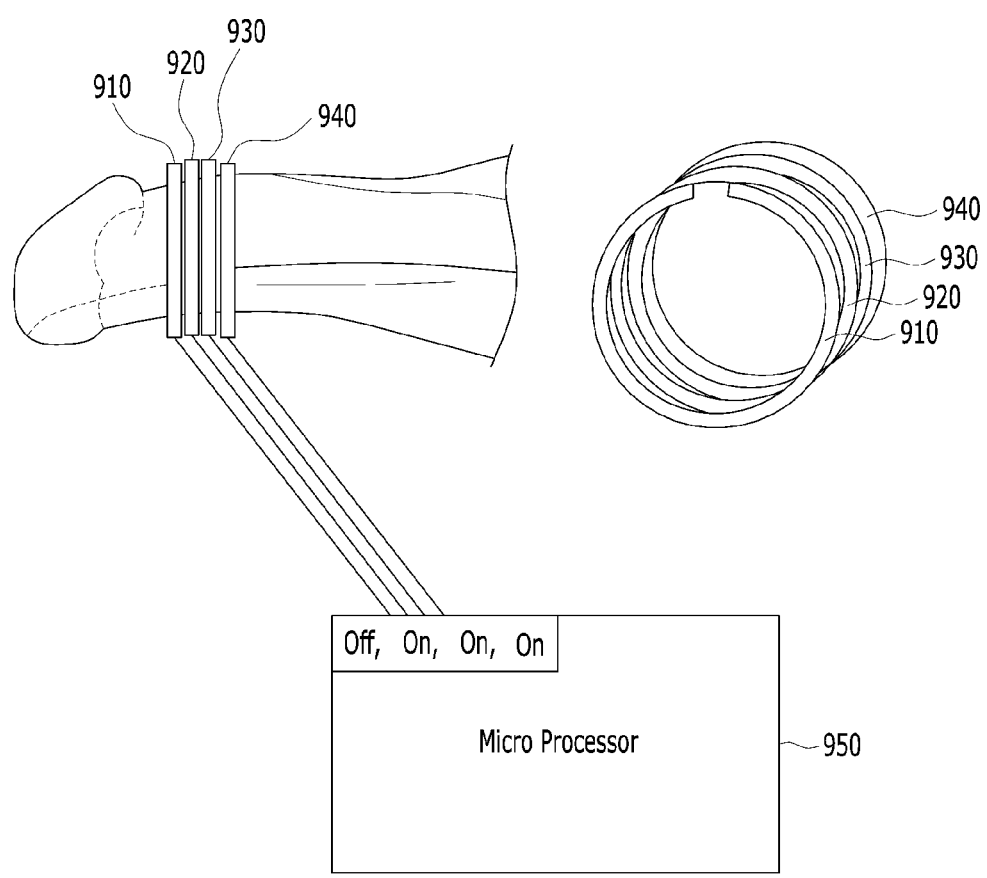
FIG. 9 is a view showing the concept of measuring a body part of a user by using progressive sensing according to another embodiment of the present invention.
Figure 10:
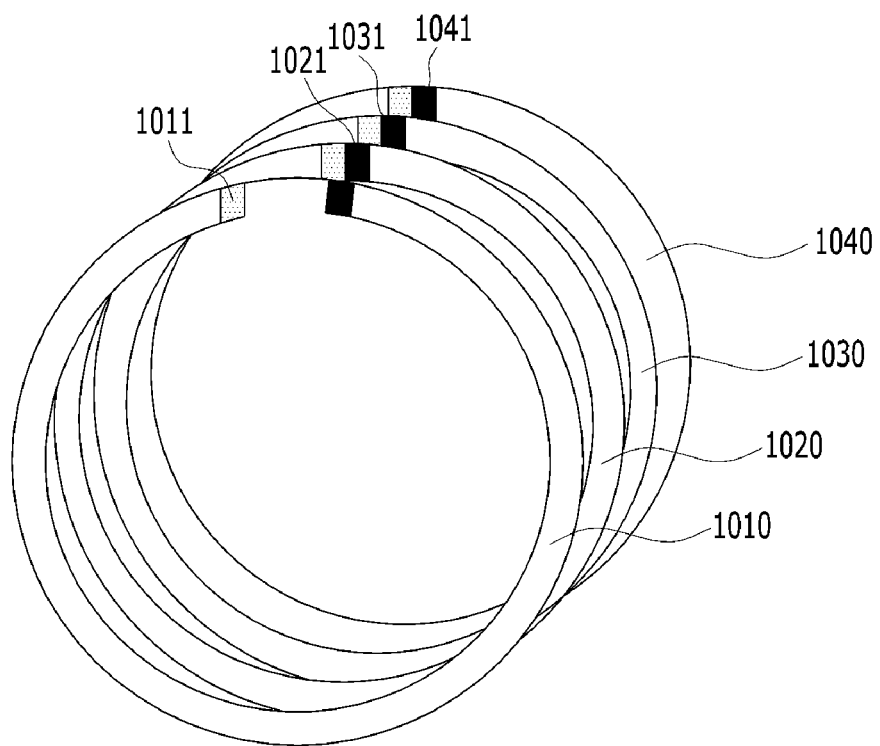
FIG. 10 is a view showing a ring-shaped progressive sensor according to an embodiment of the present invention.

FIGS. 9 and 10 are views showing the concept of measuring a body part of a user by means of progressive sensing according another embodiment of the present invention.

A progressive sensor according to an embodiment of the present invention includes one or more ring sensors 910, 920, 930 and 940 which are attached to a body part of a user such that they surround the body part and which have different lengths. Each of the ring sensors 910, 920, 930 and 940 includes a body 1010, 1020, 1030 or 1040 configured to have a gap, and a tip sensor pair 1011, 1021, 1031 or 1041 disposed at the opposite ends of the gap of the body 1010, 1020, 1030 or 1040 and configured to acquire sensor-sensed information regarding the body part of the user. Furthermore, there is provided a processor 950 configured to generate diagnostic information regarding the body part of the user based on the sensor-sensed information detected by the tip sensor pairs 1011, 1021, 1031 and 1041.

In this case, the sensor-sensed information refers to raw data detected by the sensors 910, 920, 930 and 940, such as changes in the body part of the user, or the like, data obtained by correcting raw data, or data obtained by processing raw data. The diagnostic information refers to a data set obtained by storing raw data detected by the tip sensor pairs 1011, 1021, 1031 and 1041 based on time or predetermined time intervals, or refers to data obtained by classifying raw data detected by the sensor based on occurred events and then storing the classified data. The sensor-sensed information may be generated using raw data without change, may be generated through processing, such as the conversion of raw data into format appropriate for classification, or may be generated after the correction of the measurement error of raw data using a common correction technique.

In this case, a configuration may be made such that a single sensor pair 1011, 1021, 1031 or 1041 is attached to both ends of each of the bodies 1010, 1020, 1030 and 1040.

In other words, the ends of the body of each of the sensors (tip sensor pairs) disposed the ends of the ring-shaped bodies having different lengths are separated from each other when the circumferential length of the body part of the user becomes the overall length of the body due to a change in the body part of the user. In this case, the sensor disposed at the ends of the body detects an OFF signal into which an electrical has switched from an ON signal.

Accordingly, the processor may generate diagnostic information for the diagnosis of the erectile sustainability of the specific body part (penis) of the user (subject) and the rigidity of the body part based on the sensor-sensed information detected by the sensor and sensing time, and may transfer the diagnostic information to the communication device for the purpose of the diagnosis of the erectile capability of the user (subject). In this case, the diagnostic information may be transferred to the communication device over a common communication network including a wired communication network and/or a wireless communication network. The transfer of the diagnostic information may be performed via well-known communication technology, such as TCP/IP, Wi-Fi, Bluetooth, or the like.

The communication device described herein may be a mobile communication device including a smartphone, a PDA, and a mobile phone. Alternatively, the communication device may be a wireless communication-enabled personal computer or another operation processing-enabled electronic device, other than a mobile communication device.

FIG. 10 show the sensor bodies 1010, 1020, 1030 and 1040 shown in FIG. 9 and the tip sensor pairs 1011, 1021, 1031 and 1041 each disposed at the opposite ends of each of the tip sensor pairs 1011, 1021, 1031 and 1041 in greater detail. For example, there are shown the one or more bodies 1010, 1020, 1030 and 1040 having different lengths and the tip sensor pairs 1011, 1021, 1031 and 1041 each disposed at the opposite ends of each of the one or more bodies 1010, 1020, 1030 and 1040 and configured to acquire sensor-sensed information regarding the body part of the user. The one or more bodies 1010, 1020, 1030 and 1040 having different lengths may be configured to have regular differences or slight differences, for example, in such a way that the circumferential length of the first body 1010 is 9 cm, the circumferential length of the second body 1020 is 9.3 cm, the circumferential length of the third body 1030 is 9.6 cm, and the circumferential length of the fourth body 1040 is 9.9 cm. Although the state in which the tip sensors of the first tip sensor pair 1011 disposed at both ends of the first body 1010 are spaced apart from each other and the tip sensors of each of the second tip sensor pair 1021 disposed at both ends of the second body 1020, the third tip sensor pair 1031 disposed at both ends of the third body 1030, and the fourth tip sensor pair 1041 disposed at both ends of the fourth body 1040 come into contact with each other is shown in FIG. 10 for ease of description, this is merely an embodiment of the present invention.

The bodies 1010, 1020, 1030 and 1040 of the progressive sensor according to the present invention have some elasticity, and thus both ends of each of the bodies 1010, 1020, 1030 and 1040 remain in contact with each other when external force is not applied. When both ends of each of the bodies 1010, 1020, 1030 and 1040 come into contact with each other, the opposite tip sensors of each of the tip sensor pairs 1011, 1021, 1031 and 1041 also come into contact with each other. For ease of description, the state in which the tip sensors of each of the tip sensor pairs 1011, 1021, 1031 and 1041 are in contact with each is referred to as an "ON state," and the state in which the tip sensors of each of the tip sensor pairs 1011, 1021, 1031 and 1041 are spaced apart from each other is referred to as "OFF state."

In this case, both ends of each of the bodies 1010, 1020, 1030 and 1040 having different circumferential lengths may be spaced apart from each other or come into contact with each other in response to a change in the body part of the user sequentially in connection with the other bodies.

As an embodiment, when the body part of the user is in an initial state (for example, in a normal non-expanded state), all the tip sensor pairs 1011, 1021, 1031 and 1041 may be in an ON state. Meanwhile, when the body part of the user exits from the initial state and is expanded, both ends of each of the bodies 1010, 1020, 1030 and 1040 may exit from a contact state and be spaced apart from each other sequentially in connection with the other bodies based on the different lengths of the bodies 1010, 1020, 1030 and 1040. In other words, the tip sensor pairs 1011, 1021, 1031 and 1041 each disposed at both ends of a corresponding one of the bodies 1010, 1020, 1030 and 1040 may be sequentially switched from an ON state to an OFF state.

For example, when only the first sensor pair 1011 disposed at both ends of the first body 1010 is in an OFF state and the other sensor pairs 1021, 1031 and 1041 are in an ON state, the processor 820 or 950 may acquire sensor-sensed information regarding the circumference of the body part of the user in a current state by using the states of the tip sensor pairs 1011, 1021, 1031 and 1041 and information about the circumferential lengths of the bodies 1010, 1020, 1030 and 1040.

For example, in the case where the circumferential lengths of the bodies 1010, 1020, 1030 and 1040 are implemented to be 9 cm, 9.3 cm, 9.6 cm, and 9.9 cm, respectively, as described in conjunction with the above-described embodiment, when only the first tip sensor pair 1011 disposed at both ends of the first body 1010 is in an OFF state during a measurement, it may be determined that the circumferential length of the body part of the user is smaller than 9 cm and larger than 9.3 cm.

Although the circumferential lengths of the bodies 1010, 1020, 1030 and 1040 may be designed to have regular differences as described in conjunction with the above-described embodiment, they need not be necessarily designed to have regular differences in another embodiment. It is sufficient if the circumferential length of the bodies 1010, 1020, 1030 and 1040 exhibit distinctive differences when they are arranged in their order. The circumferential lengths of the bodies 1010, 1020, 1030 and 1040 may be set to values having clinical significance by incorporating experimental results thereinto. For example, when the reference values of the circumferential length of a subject which cause a clinically significant state change are 6 cm and 9 cm, the circumferential lengths of the bodies 1010, 1020, 1030 and 1040 may be designed within the range of about 6 and about 9 cm. For example, the circumferential lengths of the bodies 1010, 1020, 1030 and 1040 may be designed to have respective values, such as 5.8 cm, 6.2 cm, 8.8 cm, and 9.2 cm.

The processor 820 or 950 may acquire a quantitative measured value regarding a change in the body of the subject by analyzing the tendency of values measured based on changes in the body of the subject over time. In this case, the quantitative measured value may be specified as a value within a predetermined error range based on the circumferential lengths of the bodies 1010, 1020, 1030 and 1040. Meanwhile, the processor 820 or 950 may derive a clinical diagnosis opinion on the change in the body of the subject through the statistical processing of the quantitative measured value or comparison with a general clinical diagnosis result. In other words, the processor 820 or 950 may determine whether the quantitative measured value will reach a clinical disease or is within a normal range based on the state of the subject through internal diagnosis logic by taking into account the quantitative measured value, the age of the subject, the presence or absence of an underlying disease, and/or the like.

The processor 820 or 950 may check whether each measured value pertains to an intended measuring target event or a value attributable to noise by analyzing the tendency of values measured based on changes in the body of subject over time. In other words, the processor 820, 950 may identify valid measured values by analyzing the tendency of measured values over time. In this case, the processor 820 or 950 may determine whether each measured value is a valid measured value by using information about the circumferential lengths of the bodies 1010, 1020, 1030 and 1040.

For example, it is assumed that the circumferential lengths of the bodies 1010, 1020, 1030 and 1040 are designed such that the length of the first body 1010 is smallest, the lengths of the second and third bodies 1020 and 1030 are sequentially larger than the length of the first body 1010, and the length of the fourth body 1040 is largest. Generally, the first tip sensor pair 1011 disposed at both ends of the shortest first body 1010 enters an OFF state first, and then the second tip sensor pair 1021, the third tip sensor pair 1031, and the fourth tip sensor pair 1041 sequentially enter an OFF state in ascending order of length.

When the first tip sensor pair 1011 of the shortest first body 1010 is in an ON state and the second tip sensor pair 1021 of the longer second body 1020 is in an OFF state, or when the second tip sensor pair 1021 is in an ON state and the third tip sensor pair 1031 of the longer third body 1030 is in an OFF state, this may be classified not as a valid measurement target event but as noise. The cause of the occurrence of the noise may be a disturbance of an electric signal of a sensor resulting from a shock attributable to the user's action, a shock attributable to force applied from the outside, static electricity, or the like.

In contrast, when noise is not temporarily measured but a noise signal continues for a predetermined or longer period, it may be determined that a problem has occurred with the hardware of the progressive sensor 810. For example, the above case may be determined to be the case where the cursor progressive sensor 810 is separated from a diagnosis target body part or a specific body of the sensor is damaged due to the large movement of a subject. The processor 820 or 950 may detect the failure of the progressive sensor 810, the error of the progressive sensor 810, the separation of the progressive sensor 810 from the body part of the subject, etc. by incorporating information about the circumferential lengths of the bodies 1010, 1020, 1030 and 1040 and the tendency of measured value over time.

Although the case where the ring-shaped bodies 1010, 1020, 1030 and 1040 constituting the progressive sensor 810 have different circumferential lengths is shown in FIG. 10, the technical spirit of the present invention is not limited thereto, but an embodiment in which the bodies 1010, 1020, 1030 and 1040 have different elastic coefficients and react to changes in the circumferential length of the body part at different threshold values.

Figure 11:
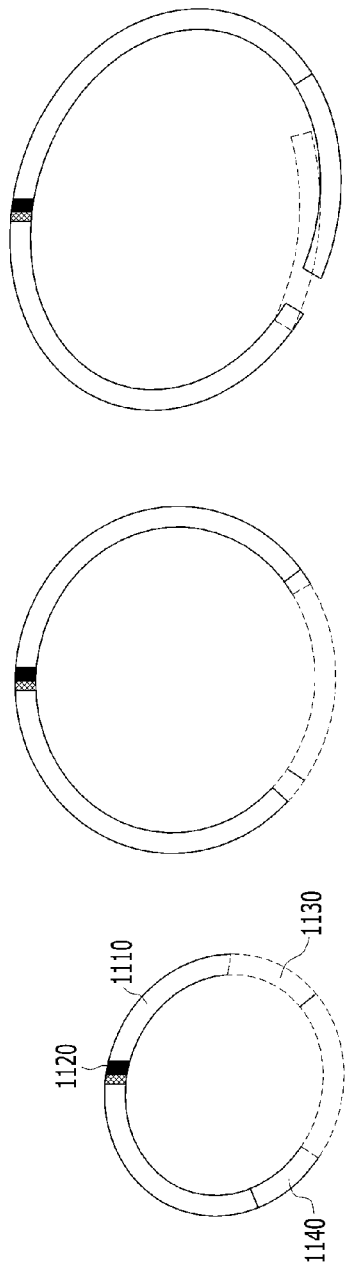
FIG. 11 is a view showing a length-adjustable ring-shaped progressive sensor according to another embodiment of the present invention.

FIG. 11 is a view showing a length-adjustable ring-shaped progressive sensor according to another embodiment of the present invention.

As shown in FIG. 11, the length of at least one body 1110 may be adjusted to suit the body part of the user by using Velcro or elastic material.

For example, when Velcro is used, a female Velcro member 1130 and a male Velcro member 1140 may be disposed on a side opposite to both ends of the body 1110 where sensors 1120 are disposed, and a diagnosis expert may directly adjust the length of the body 1110 to suit the shape the body part of the user by means of the female Velcro member 1130 and the male Velcro member 1140 and then install the progressive sensor on the body part of the user.

In this case, although the shape of the body part of the user may be the circumferential length of the body part of the user, it may incorporate an unusual shape when the body part of the user has the unusual shape.

Accordingly, the processor 820 or 950 may generate diagnostic information by means of sensor-sensed information regarding the body part of the user based on the length of the Velcro adjusted before the start of a test for the body part of the user. Alternatively, the processor 820 or 950 may receive generated diagnostic information from a communication device, and may diagnose the health state of the user by using the previously adjusted length of the Velcro.

Referring to FIGS. 5 and 9 to 11, FIG. 5 may be also applied to a display screen configured to visualize a penile tumescence sensing signal of each of the progressive sensors according to the embodiments of FIGS. 9 to 11 and then provide visualized information to a user.

Figure 12:
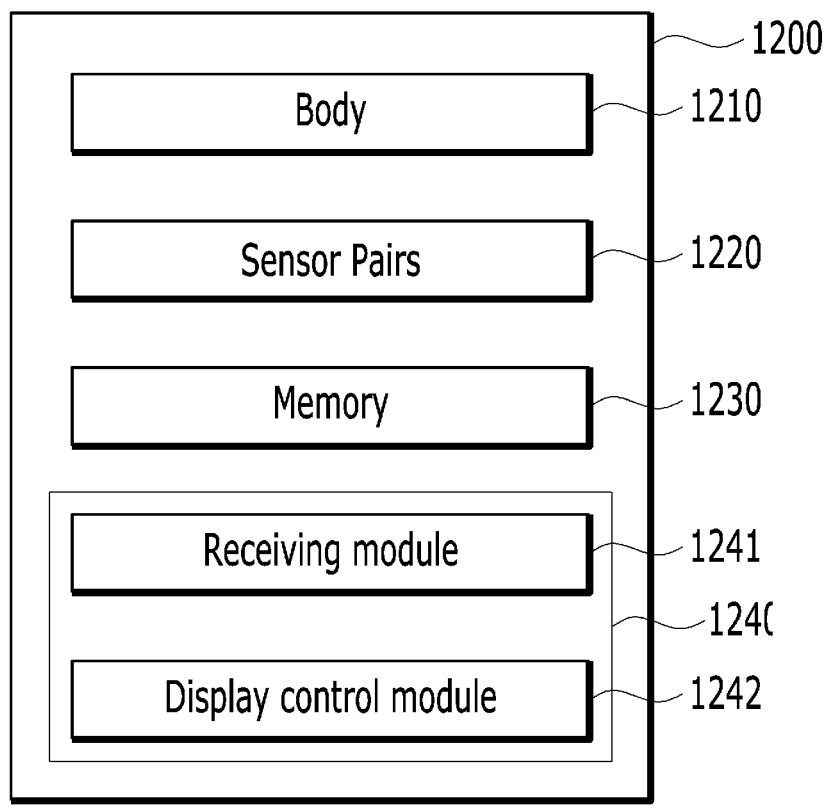
FIG. 12 is a block diagram showing a progressive sensing-based penile tumescence diagnosis device according to another embodiment of the present invention.

FIG. 12 is a block diagram showing a progressive sensing-based penile tumescence diagnosis device according to another embodiment of the present invention.

The progressive sensing-based penile tumescence diagnosis device includes one or more bodies 1210, one or more sensor pairs 1220, memory 1230, and a processor 1230. The processor 1230 includes a receiving module 1241, and a display control module 1242.

The one or more bodies 1210 are attached to a body part of a user so that they surround the body part of the user in a ring shape, and are characterized by having different lengths.

The one or more sensor pairs 1220 are each disposed at the opposite ends of each of the one or more bodies 1210, and acquire sensor-sensed information regarding the body part of the user. In this case, the sensor-sensed information refers to raw data obtained by detecting changes in the circumference of the body part of the user or the like, or refers to data obtained by processing/correcting raw data. Each of the sensor pairs 1220 may include a single sensor pair mounted on a corresponding one of the bodies 1210.

Furthermore, the sensor pairs 1220 may acquire sensor-sensed information in a sequential or stepwise manner as the one or more bodies 1210 are individually deformed in response to changes in the body part of the user. Accordingly, measurement may be performed based on the different lengths of the bodies 1210 in a stepwise manner.

The processor 1230 generates diagnostic information regarding the body part of the user based on the sensor-sensed information regarding the body part of the user detected by the sensor pairs 1220. In this case, the diagnostic information refers to a data set obtained by storing raw data, obtained by detecting changes in the circumference of the body part of the user, based on time or predetermined time intervals, or refers to data obtained by classifying raw data based on specific events and then storing the classified data.

The memory 1230 stores the sensor-sensed information detected by the sensor pairs 1220 based on sensing time. In this case, the receiving module 1241 included in the processor 1240 receives the detected sensor-sensed information from the sensor pairs 1220.

Accordingly, the processor 1240 may generate diagnostic information regarding the body part of the user based on the sensor-sensed information stored in the memory 1230 based on the sensing time.

Furthermore, the processor 1240 may detect one or more occurred events from the sensor pairs 1220 based on the sensor-sensed information regarding the body information user, and may generate diagnostic information regarding the body part based on the lengths of the bodies corresponding to the sensor pairs 1220. In this case, each of the occurred events refers to the case where the sensor elements of the sensor pair 1220 connected to a corresponding one of the bodies 1210 are spaced apart from each other in response to a change in the body part of the user (i.e., an OFF state). The state where the sensor elements of the corresponding sensor pair 1220 are spaced apart from each other (an ON state) and the state where the sensor elements of the corresponding sensor pair 1220 are not spaced apart from each other (an OFF state) may be defined for each of the bodies 1210 having different lengths. The processor may generate diagnostic information based on the length of the body 1210 in which an event has occurred in the sensor pair 1220 thereof.

In this case, the one or more bodies 1210 may be attached to a body part of a user so that they surround the body part in a ring shape, with the length of each of the one or more bodies 1210 having been adjusted to suit the shape of the body part of the user. The shape of the body part of the user does not only refer to only the circumferential length of the body part of the user, but also incorporates the unusual shape of the body part of the user when the body part has the unusual shape. The lengths of the one or more bodies 1210 may be adjusted by taking into account not only the circumferential length but also the unusual shape.

Furthermore, the processor 1240 may detect one or more valid events from the sensor-sensed information acquired by the sensor pairs 1220, and may generate body information regarding the body part of the user based on the pattern of the sensor-sensed information corresponding to the detected valid events.

In other words, the case where the ends of bodies 1210 having different lengths are opened in a stepwise or sequential manner in response to changes in the body of the user over time during a test period may be considered to be a valid event. In contrast, the case where the ends of the first body are opened and then the ends of the third body are opened before the opening of the ends of the second body may be considered to be an event attributable to a shock applied by the user or an external shock. This event may be classified not as a valid event but as noise.

The display control module 1242 included in the processor 1240 functions to visualize the sensor-sensed information, stored in the memory 1230, based on sensing time.

The display module 1242 may display both the sensor-sensed information and the health state of the body part of the user based on sensing time according to information about the user. In this case, the information about the user includes the personal data of the user, a habit which may influence the health of the user, the presence or absence of a disease, a past medical history, a past diagnosis record, an administration record, the presence or absence of hypertension, the presence or absence of diabetes, and/or the like. It may be possible to display a determination result, together with a valid event, noise, a comment indicating that the user is healthy, and/or the like for each portion of the sensor-sensed information of the user in which it is determined that a main event has occurred, based on sensing time.

Figure 13:
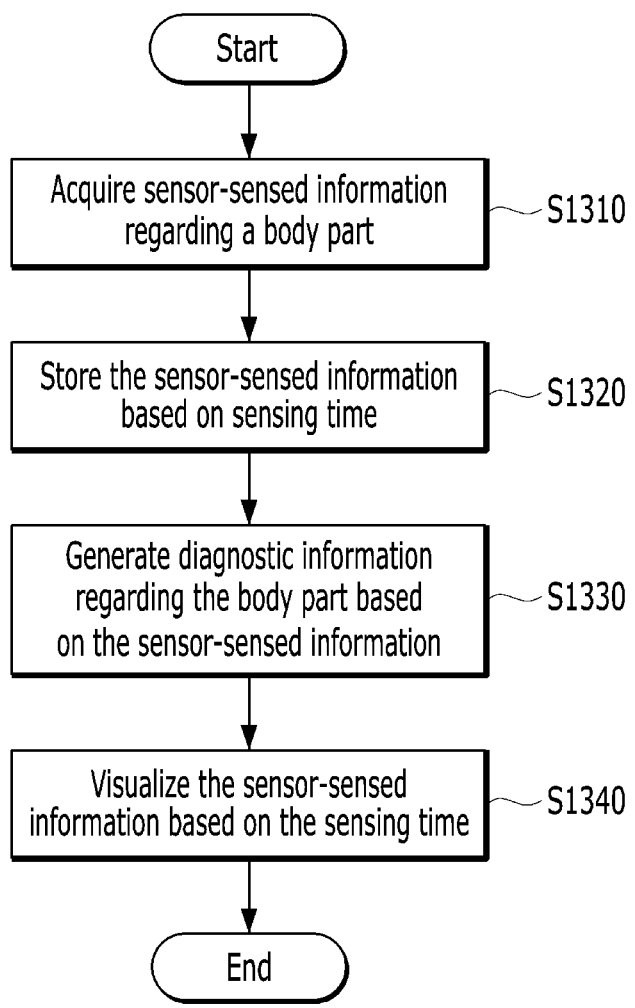
FIG. 13 is an operation flowchart showing a progressive sensing-based penile tumescence diagnosis method according to another embodiment of the present invention.

FIG. 13 is an operation flowchart showing a progressive sensing-based penile tumescence diagnosis method according to another embodiment of the present invention.

The progressive sensing-based penile tumescence diagnosis method according to the embodiment of the present invention includes: step S1310 of acquiring sensor-sensed information regarding a body part of a user from sensors attached to the body part of the user such that they surround the body part of the user in a ring shape and each disposed at the opposite ends of each of one or more bodies having different lengths; and step S1320 of generating diagnostic information regarding the body part of the user based on the sensor-sensed information detected by the sensors.

Furthermore, the sensors may acquire sensor-sensed information in a sequential or stepwise manner as the one or more bodies are individually deformed in response to changes in the body part of the user. Accordingly, measurement may be performed based on the different lengths of the bodies in a stepwise manner.

Furthermore, diagnostic information regarding the body part of the user is generated based on the sensor-sensed information regarding the body part of the user detected by the sensors. In this case, the diagnostic information refers to a data set obtained by storing raw data, obtained by detecting changes in the circumference of the body part of the user, based on time or predetermined time intervals, or refers to data obtained by classifying raw data based on specific events and then storing the classified data.

Furthermore, the sensor-sensed information detected by the sensors may be stored based on sensing time at step S1330, and diagnostic information regarding the body part of the user may be generated based on the stored sensor-sensed information based on the sensing time.

Furthermore, one or more occurred events may be detected from the sensors based on the sensor-sensed information regarding the body information user, and diagnostic information regarding the body part may be generated based on the lengths of the bodies corresponding to the sensors. In this case, each of the occurred events refers to the case where the sensor elements of the sensor connected to a corresponding one of the bodies are spaced apart from each other in response to a change in the body part of the user (i.e., an OFF state). The state where the sensor elements of the corresponding sensor are spaced apart from each other (an ON state) and the state where the sensor elements of the corresponding sensor are not spaced apart from each other (an OFF state) may be defined for each of the bodies having different lengths. Diagnostic information may be generated based on the lengths of the bodies of the sensors in which an event has occurred.

In this case, the one or more bodies may be attached to a body part of a user so that they surround the body part in a ring shape, with the length of each of the one or more bodies having been adjusted to suit the shape of the body part of the user. The shape of the body part of the user does not only refer to only the circumferential length of the body part of the user, but also incorporates the unusual shape of the body part of the user when the body part has the unusual shape. The lengths of the one or more bodies may be adjusted by taking into account not only the circumferential length but also the unusual shape.

Furthermore, one or more valid events may be detected from the sensor-sensed information acquired by the sensors, and body information regarding the body part of the user may be generated based on the pattern of the sensor-sensed information, i.e., the width of a pulse (erectile duration), and a peak value (the circumferential length of a penis), corresponding to the detected valid events.

In other words, the case where the ends of bodies 1210 having different lengths are opened in a stepwise or sequential manner in response to changes in the body of the user over time during a test period may be considered to be a valid event. In contrast, the case where the ends of the first body are opened and then the ends of the third body are opened before the opening of the ends of the second body may be considered to be an event attributable to a shock applied by the user or an external shock. This event may be classified not as a valid event but as noise.

Furthermore, the stored sensor-sensed information may be visualized based on sensing time step S1340. In this case, both the sensor-sensed information and the health state of the body part of the user may be displayed based on sensing time according to information about the user. The information about the user includes all contextual information which needs to be additionally taken into account when the specific body part of the user is diagnosed, as described above. For example, the information about the user refers to information including the personal data of the user, a habit (drinking, or smoking) which may influence the health of the user, the presence or absence of a disease, a past medical history, a past diagnosis record, whether a medicine is being administered or not, and/or the like, as described above. It may be possible to display a determination result, together with a valid event, noise, the comment "Your are healthy," and/or the like for each portion of the sensor-sensed information of the user in which it is determined that a main event has occurred, based on sensing time.

Figure 16:
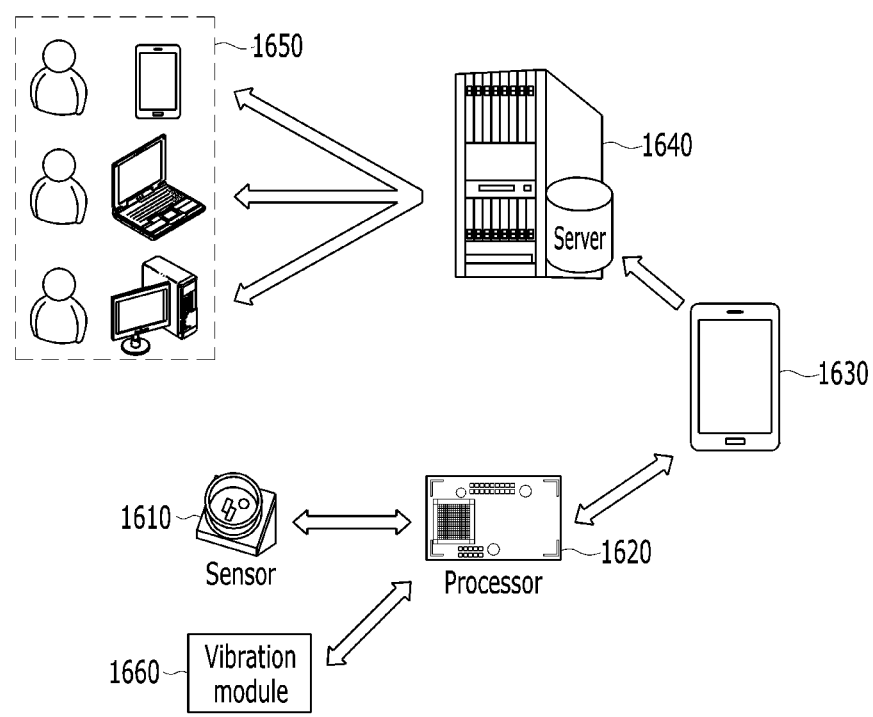
FIG. 16 is a view showing a penile tumescence diagnosis system according to still another embodiment of the present invention.

FIG. 16 is a view showing a penile tumescence diagnosis system according to still another embodiment of the present invention.

Since the sensor 1610, processor 1620, communication device 1630 and server 1640 of FIG. 16 are similar in function to the sensor 810, processor 820, communication device 830 and server 840 of FIG. 8, redundant descriptions are omitted. A description of users or doctors 1650 is omitted in the same manner.

The vibration module 1660 of FIG. 16 generates a vibration stimulus, thereby stimulating a body part to which the user sensor 1610 has been attached and also inducing a change in the body part. The vibration stimulus may increase the measured samples of the sensor 1610 within a short time by inducing a change in the body part. Accordingly, measuring time is decreased, and the intervals between phenomena are kept uniform, thereby further improving the reliability of measurement.

In other words, when the intervals between occurrences are excessively irregular and the occurrence of penile tumescence is not easy, long-term observation is required to ensure measured samples. When the intervals between occurrences are excessively long, the reliability of measurement may be degraded. Accordingly, when an appropriate number of measured samples are not ensured during a predetermined or longer period, a number of changes in the body part sufficient to ensure an appropriate number of measured samples may be induced.

Figure 14:
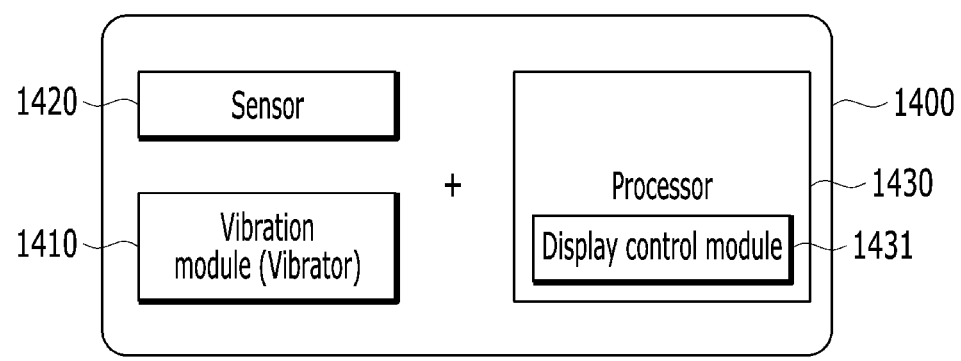
FIG. 14 is a view showing a vibration stimulus-based penile tumescence diagnosis device according to still another embodiment of the present invention.

FIG. 14 is a view showing a vibration stimulus-based penile tumescence diagnosis device 1400 according to still another embodiment of the present invention.

The vibration stimulus-based penile tumescence diagnosis device 1400 according to the embodiment of the present invention includes a vibration module 1410, a sensor 1420, and a processor 1430. The processor 1430 includes a display control module 1431.

The vibration module 1410 is attached to a body part of a user, and functions to help an erection of the user by applying a vibration stimulus to the body part of the user.

The sensor 1420 is attached to the body part of the user, and acquires sensor-sensed information regarding the body part of the user based the vibration stimulus applied by the vibration module 1410 and time. In this case, the sensor-sensed information refers to raw data obtained by detecting changes in the circumference of the body part of the user or the like, or refers to data obtained by processing/correcting raw data.

The processor 1430 controls the vibration module 1410 such that the vibration module 1410 applies a stimulus to the body part of the user, and generates diagnostic information regarding the body part of the user based on the sensor-sensed information detected by the sensor 1420. In this case, the diagnostic information refers to a data set obtained by storing raw data, obtained by detecting changes in the circumference of the body part of the user, based on time or predetermined time intervals, or refers to data obtained by classifying raw data based on specific events and then storing the classified data. The sensor-sensed information may be generated using raw data without change, may be generated through processing, such as the conversion of raw data into format appropriate for classification, or may be generated after the correction of the measurement error of raw data using a common correction technique.

Accordingly, the processor 1430 may generate diagnostic information for the diagnosis of the erectile sustainability of the specific body part (penis) of the user (subject) and the rigidity of the body part based on the sensor-sensed information detected by the sensor and sensing time, and may transfer the diagnostic information to the communication device for the purpose of the diagnosis of the erectile capability of the user (subject). In this case, the diagnostic information may be transferred to the communication device over a common communication network including a wired communication network and/or a wireless communication network. The transfer of the diagnostic information may be performed via well-known communication technology, such as TCP/IP, Wi-Fi, Bluetooth, or the like.

The communication device described herein may be a mobile communication device including a smartphone, a PDA, and a mobile phone. Alternatively, the communication device may be a wireless communication-enabled personal computer or another operation processing-enabled electronic device, other than a mobile communication device.

Furthermore, the processor 1430 may control the strength and duration of the vibration module 1410 and the time intervals at which vibrations of the vibration module 1410 are applied, based on the sensor-sensed information detected by the sensor 1420, may control the strength and duration of the vibration module 1410 and the time intervals at which vibrations of the vibration module 1410 are applied, based on previously stored information about the user, or may control the strength and duration of the vibration module 1410 and the time intervals at which vibrations of the vibration module 1410 are applied, based on both the sensor-sensed information and information about a user. In this case, the information about the user refers to the personal data of the user, a habit which may influence the health of the user, the presence or absence of a disease, a past medical history, a past diagnosis record, blood pressure, blood glucose, the presence or absence of a specific disease (hypertension, diabetes, or the like), and/or the like.

In other words, when the body part of the user is stimulated by the vibration module 1410, the processor 1430 may generate diagnostic information for a diagnosis of a psychogenic problem or organic problem in response to the reaction of the body part of the user based on sensing time.

Furthermore, the processor 1430 may detect one or more valid events from the sensor-sensed information acquired by the sensor 1420, and may generate diagnostic information for a diagnose the health state of the specific body part of the user attributable to the erectile duration and circumferential length of the penis of a typical adult man based on the pattern of the sensor-sensed information, i.e., the width of a pulse (erectile duration), and a peak value (the circumferential length of a penis), corresponding to the detected valid events.

The display control module 1431 included in the processor 1430 may visualize the sensor-sensed information, detected by the sensor 1420, based on sensing time. In this case, it may be possible to display the sensor-sensed information and the health state of the body part of the user based on sensing time for each portion of the sensor-sensed information in which a main event occurs, along with a determination result, i.e., a valid event, noise, a comment indicating a healthy state, and/or the like, according to the information about the user. In this case, the information about the user refers to the personal data of the user, a habit which may influence the health of the user, the presence or absence of a disease, a past medical history, a past diagnosis record, blood pressure, blood glucose, the presence or absence of a specific disease (hypertension, diabetes, or the like), and/or the like.

In still another embodiment of the present invention, the processor 1430 may receive the strength and duration of the vibration module 1410 and the time intervals at which vibrations of vibration module 1410 are applied directly from the user, and may then control the vibration module 1410.

The present invention is directed to a diagnosis device designed to diagnose whether an organic disease is present in a specific body part of a user. Accordingly, there is a need to deal with the case where a tumescent event which occurs in normal men three to five times during sleep may not occur easily in a diagnostic subject of the present invention. The diagnosis device according to the present invention includes the vibration module 1410 in addition to basic function components for diagnosis, such as the processor 1430 and the sensor 1420, thereby providing the effects of facilitating a diagnosis of nocturnal unconscious penile tumescence in a sleep state and increasing the range of subjects which can be diagnosed.

As described above, the causes of erectile dysfunction include various ones, such as a psychogenic problem, an organic problem, and a combination thereof. The aspects of the causes which appear in patients in practice are more complex.

According to the present invention, the processor 1430 may primarily make a diagnosis via night measurement without the operation of the vibration module 1410, and may determine whether to operate the vibration module 1410 based on the aspect of the diagnosis of a subject. Furthermore, at least one of an organic factor and a psychogenic factor may be effectively excluded or may be diagnosed as being dominant by using the differences between a diagnosis result when the vibration module 1410 operates and a diagnosis result when the vibration module 1410 does not operate.

When the reaction of a body part subjected to a vibration stimulus applied by the operation of the vibration module 1410 and the reaction of the body part diagnosed in normal mode with the operation of the vibration module 1410 are different from each other, the processor 1430 may effectively specify a diagnosis on the state of a subject based on these diagnosis results. Furthermore, the processor 1430 may quantitatively evaluate the reaction of the body part subjected to the vibration stimulus applied by the operation of the vibration module 1410, thereby quantitatively evaluating the seriousness of the organic problem or psychogenic problem of the subject.

The technical spirit of the present invention is characterized by the process of deriving advanced diagnostic information through the cooperative operation of the processor 1430, the vibration module 1410, and the sensor 1420. In other words, the vibration module 1410 operates in cooperation with the processor 1430. When the diagnosis result of the sensor 1420 is influenced by the vibration module 1410, the influence may be quantitatively evaluated. Furthermore, the processor 1430 may include logic configured to derive more advanced diagnostic information by integrating the frequency/strength of the operation of the vibration module 1410 and information about the context of operation of the vibration module 1410. The processor 1430 may derive qualitative diagnostic information regarding the state of the body part of the subject based on the difference between the diagnosis results of the sensor 1420 attributable to whether the vibration module 1410 operates or not. The qualitative diagnostic information may include an evaluation about which of the organic and psychogenic factors is dominant.

The vibration module 1410 may be implemented in the form of a vibrator configured to generate vibrations by means of operation of a motor, or in the form of a module configured to generate vibrations attributable to pressure differences by applying electrical stimuli to a piezoelectric unit. A well-known vibration generation technology may be used as the technique of generating the vibrations of the vibration module 1410. The use of the well-known vibration generation technology within the technical spirit of the present invention will be apparent to those skilled in the art based on the description of the present specification.

Figure 15:
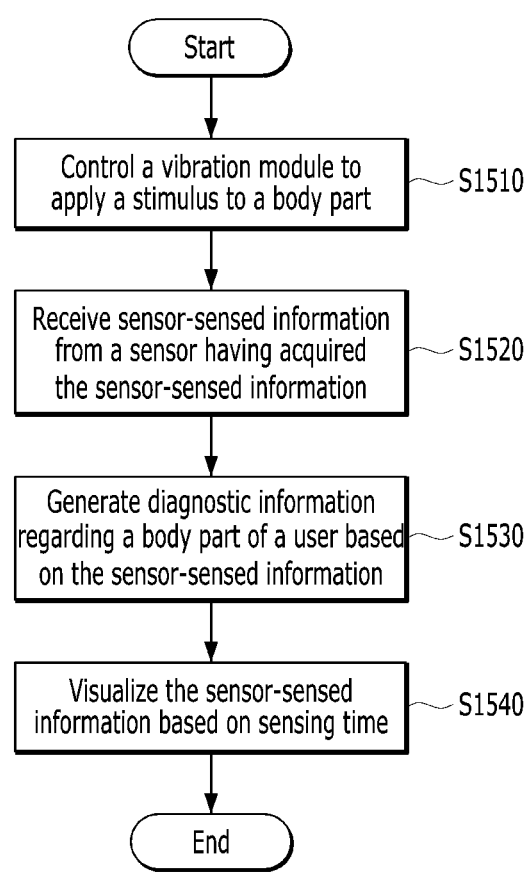
FIG. 15 is an operation flowchart showing a vibration stimulus-based penile tumescence diagnosis method according to still another embodiment of the present invention.

FIG. 15 is an operation flowchart showing a vibration stimulus-based penile tumescence diagnosis method according to still another embodiment of the present invention.

The vibration stimulus-based penile tumescence diagnosis method according to the embodiment of the present invention may include step S1510 of controlling a vibration module attached to a body part of a user such that the vibration module helps an erection of the user by applying a vibration stimulus to the body part of the user.

Thereafter, sensor-sensed information regarding the body part of the user based on the vibration stimulus applied by the vibration module and time is acquired from a sensor attached to the body part of the user at step S1520. In this case, the sensor-sensed information refers to raw data obtained by detecting changes in the circumference of the body part of the user or the like.

Thereafter, diagnostic information regarding the body part of the user is generated based on the sensor-sensed information detected by the sensor by controlling the vibration module such that the vibration module applies a stimulus to the body part of the user at step S1530. In this case, the diagnostic information refers to a data set obtained by storing raw data, obtained by detecting changes in the circumference of the body part of the user, based on time or predetermined time intervals, or refers to data obtained by classifying raw data based on specific events and then storing the classified data.

Accordingly, diagnostic information for the diagnosis of the erectile sustainability of the specific body part (penis) of the user (subject) and the rigidity of the body part may be generated based on the sensor-sensed information detected by the sensor and sensing time, and the diagnostic information may be transferred to the communication device for the purpose of the diagnosis of the erectile capability of the user (subject).

Furthermore, the strength and duration of the vibration module 1410 and the time intervals at which vibrations of the vibration module 1410 are applied may be controlled based on the sensor-sensed information detected by the sensor 1420, may be controlled based on previously stored information about the user, or may be controlled based on both the sensor-sensed information and information about a user. In this case, the information about the user refers to the personal data of the user, a habit which may influence the health of the user, the presence or absence of a disease, a past medical history, a past diagnosis record, blood pressure, blood glucose, the presence or absence of a specific disease (hypertension, diabetes, or the like), and/or the like.

In other words, when the body part of the user is stimulated by the vibration module, diagnostic information for a diagnosis of a psychogenic problem or organic problem may be generated in response to the reaction of the body part of the user based on sensing time.

Furthermore, the sensor-sensed information detected by the sensor may be visualized based on sensing time at step S1540. In this case, it may be possible to display the sensor-sensed information and the health state of the body part of the user based on sensing time for each portion of the sensor-sensed information in which a main event occurs, along with a determination result, i.e., a valid event, noise, a comment indicating a healthy state, and/or the like, according to the information about the user. In this case, the information about the user refers to the personal data of the user, a habit which may influence the health of the user, the presence or absence of a disease, a past medical history, a past diagnosis record, blood pressure, blood glucose, the presence or absence of a specific disease (hypertension, diabetes, or the like), and/or the like.

In still another embodiment of the present invention, the strength and duration of the vibration module 1410 and the time intervals at which vibrations of vibration module 1410 are applied may be received directly from the user, and then the vibration module may be controlled.

The present invention was derived from the research conducted under the sponsorship of the Korean Ministry of Science, ICT and Future Planning and the National Research Foundation of Korea [Task Serial Number: 0414-20150019; Research Project Name: Support for New Researchers; Task Name: Cost-effective Electronic Information Technology for Multiscale Omics].

The penile tumescence diagnosis method according to the embodiment of the present invention may be implemented in the form of program instructions which can be executed by a variety of computer means, and may be stored in a computer-readable storage medium. The computer-readable storage medium may include program instructions, a data file, and a data structure solely or in combination. The program instructions which are stored in the medium may be designed and constructed particularly for the present invention, or may be known and available to those skilled in the field of computer software. Examples of the computer-readable storage medium include magnetic media such as a hard disk, a floppy disk and a magnetic tape, optical media such as CD-ROM and a DVD, magneto-optical media such as a floptical disk, and hardware devices particularly configured to store and execute program instructions such as ROM, RAM, and flash memory. Examples of the program instructions include not only machine language code which is constructed by a compiler but also high-level language code which can be executed by a computer using an interpreter or the like. The above-described hardware components may be configured to act as one or more software modules which perform the operation of the present invention, and vice versa.

According to the present invention, the diagnosis device which can be fabricated in small size and light weight and implemented at low cost can be implemented through the improvement of a diagnosis device which measures the nocturnal penile tumescence during sleep. According to the present invention, the short-range communication-based diagnosis device can be implemented using a sensor and a communication device, and thus the volume of the diagnosis device can be reduced, thereby enabling nocturnal penile tumescence to be measured during sleep without disturbing the sleep of a user (subject). According to the present invention, the progressive sensing-based penile tumescence diagnosis device can be implemented, and thus the volume of the diagnosis device can be reduced, thereby enabling nocturnal penile tumescence to be measured during sleep without disturbing the sleep of a user (subject).

Furthermore, the present invention is advantageous in that there can be implemented the penile tumescence diagnosis device which can be fabricated in small sized and light weight and implemented at low cost, and is also advantageous in that data can be stored in a specific server in real time by means of a communication device, thereby reducing the loss of data.

Furthermore, the present invention is advantageous in that a motor for measuring the circumference and rigidity of a body part of a user is not employed, thereby making the diagnosis device small and lightweight, reducing battery consumption attributable to the use of a motor, and also reducing noise.

The present invention is advantageous in that the information generated by the diagnostic diagnosis device can be stored in a specific server in real time by means of a communication device, thereby reducing the loss of data.

The present invention is advantageous in that the states of a plurality of subjects can be diagnosed at one time via a single communication device by generating diagnostic information by using sensing signals detected by sensors attached to two or more subjects (users) and transferring the diagnostic information to the communication device.

Furthermore, the present invention is advantageous in that the personal data of a user, a habit which may influence health, the presence or absence of a disease, a past medical history, and a past diagnosis record can be previously stored in the communication device according to the present invention and then the health state of a body part of the user can be more accurately diagnosed by using a sensing signal detected by the sensor, together with the previously stored information about the user.

Furthermore, according to the present invention, the vibration stimulus-based penile tumescence diagnosis device can be implemented, thus the volume of the diagnosis device can be reduced, thereby enabling nocturnal penile tumescence to be measured during sleep without disturbing the sleep of a user (subject).

Moreover, according to the present invention, a stimulus can be applied to a body part of a user during sleep by means of the vibration module, thereby reducing measuring time and also enabling more accurate measurement.

While the present invention has been described in conjunction with specific details, such as specific elements, and the limited embodiments and diagrams above, these are provided merely to help an overall understanding of the present invention. The present invention is not limited to these embodiments, and various modifications and alterations may be made based on the foregoing description by a person having ordinary knowledge in the art to which the present invention pertains.

Therefore, the technical spirit of the present invention should not be determined based on only the described embodiments, and the following claims, all equivalents to the claims and equivalent modifications should be construed as falling within the scope of the spirit of the present invention.

What is claimed is:

1. A penile tumescence diagnosis device, comprising:
a plurality of ring sensors configured to measure a circumference of a body part of a user and generate sensor-sensed information, wherein the body part is a penis; and
a processor configured to generate diagnostic information regarding the body part of the user based on the sensor-sensed information generated by the plurality of ring sensors;
wherein the plurality of ring sensors comprises:
    a first ring sensor configured to have a first threshold length regarding the circumference of the body part and be disposed on the body part to surround the body part in a ring shape; and
    a second ring sensor configured to have a second threshold length regarding the circumference of the body part larger than the first threshold length and be disposed on the body part to surround the body part in a ring shape;
wherein the first ring sensor comprises a ring-shaped first body formed such that both ends thereof are configured to be spaced apart from each other, and a first tip sensor pair disposed at the both ends of the first body, the first body has a first elasticity corresponding to the first threshold length;
wherein the second ring sensor comprises a ring-shaped second body formed such that both ends thereof are configured to be spaced apart from each other, and a second tip sensor pair disposed at the both ends of the second body, the second body has a second elasticity corresponding to the second threshold length;
wherein the first tip sensor pair determines whether elements of the first tip sensor pair are in contact with each other or spaced apart from each other in response to a first electrical signal between the elements of the first tip sensor pair resulting from a change in the circumference of the body part and generates first state information whether the elements of the first tip sensor pair are in contact with each other or spaced apart from each other, and the second tip sensor pair determines whether elements of the second tip sensor pair are in contact with each other or spaced apart from each other in response to a second electrical signal between the elements of the second tip sensor pair resulting from the change in the circumference of the body part and generates second state information whether the elements of the second tip sensor pair are in contact with each other or spaced apart from each other;
wherein the sensor-sensed information generated by the plurality of ring sensors includes the first state information generated by the first tip sensor pair and the second state information generated by the second tip sensor pair; and
wherein the processor is further configured to:
    derive a first comparison result between the circumference of the body part and the first threshold length and a second comparison result between the circumference of the body part and the second threshold length based on the first state information and the second state information; and
    sequentially determine a switch between an ON state and an OFF state in the first state information of the first tip sensor pair and a switch between an ON state and an OFF state in the second state information of the second tip sensor pair based on the first comparison result and the second comparison result in response to the change in the circumference of the body part.

2. The penile tumescence diagnosis device of claim 1, wherein the processor is further configured to:
    determine whether a sequence of the switch in the first state information and the switch in the second state information matches a predetermined sequence; and
    determine whether the sensor-sensed information of the sensors is valid based on whether the sequence of the switch in the first state information and the switch in the second state information matches the predetermined sequence.

3. The penile tumescence diagnosis device of claim 1, further comprises:
    memory configured to store the sensor-sensed information detected by the plurality of ring sensors based on sensing time;
    wherein the processor is further configured to:
        receive the sensor-sensed information detected by the plurality of ring sensors; and
        generate the diagnostic information regarding the body part based on the sensor-sensed information stored in the memory based on the sensing time.

4. The penile tumescence diagnosis device of claim 3, wherein the processor further configured to visualize the sensor-sensed information stored in the memory based on the sensing time on a display.

5. The penile tumescence diagnosis device of claim 4, wherein the processor is further configured to visualize both the sensor-sensed information and a health state of the body part based on the sensing time according to information about the user on the display.

6. The penile tumescence diagnosis device of claim 1, wherein the first body and the second body are attached to the body part of the user to surround the body part of the user in a ring shape, with a length of each of the first body and the second body adjusted to suit a shape of the body part of the user.

7. The penile tumescence diagnosis device of claim 1, wherein the processor is further configured to:
    determine whether the sensor-sensed information corresponds to a valid event based on a duration and peak value of a sensing signal included in the sensor-sensed information;
    when the sensor-sensed information corresponds to a valid event, generate body information regarding the body part based on the sensor-sensed information; and
    when a case where the sensor-sensed information does not correspond to a valid event occurs successively, determine whether one or more of the sensors have failed, have caused error, or have been separated from the body part.

8. A penile tumescence diagnosis method, the penile tumescence diagnosis method being performed by a diagnosis apparatus including a processor, the penile tumescence diagnosis method comprising:
    measuring, by a plurality of ring sensors, a circumference of a body part of a user, and generating, by the plurality of ring sensors, sensor-sensed information, wherein the body part is a penis; and
    generating, by the processor, diagnostic information regarding the body part of the user based on the sensor-sensed information;
    wherein the generating, by the plurality of ring sensors, sensor-sensed information comprises:

generating, by a first tip sensor pair which is disposed at both ends of a ring-shaped first body configured to have a first threshold length regarding the circumference of the body part and to be disposed on the body part to surround the body part in a ring shape and formed such that the both ends thereof are configured to be spaced apart from each other, first state information regarding whether elements of the first tip sensor pair are in contact with each other or spaced apart from each other in response to a first electrical signal between the elements of the first tip sensor pair resulting from a change in the circumference of the body part; and generating, by a second tip sensor pair which is disposed at both ends of a ring-shaped second body configured to have a second threshold length regarding the circumference of the body part larger than the first threshold length and to be disposed on the body part to surround the body part in a ring shape and formed such that the both ends thereof are configured to be spaced apart from each other, second state information regarding whether elements of the second tip sensor pair are in contact with each other or spaced apart from each other in response to a second electrical signal between the elements of the second tip sensor pair configured from the change in the circumference of the body part;

wherein the generating, by the processor, diagnostic information comprises:

deriving a first comparison result between the circumference of the body part and the first threshold length and a second comparison result between the circumference of the body part and the second threshold length based on the first state information and the second state information; and sequentially determining a switch between an ON state and an OFF state in the first state information of the first tip sensor pair and a switch between an ON state and an OFF state in the second state information of the second tip sensor pair based on the first comparison result and the second comparison result in response to the change in the circumference of the body part.

9. The penile tumescence diagnosis method of claim 8, wherein the generating, by the processor, diagnostic information comprises:

determining whether a sequence of the switch in the first state information and the switch in the second state information matches a predetermined sequence; and determining whether the sensor-sensed information of the sensors is valid based on whether the sequence of the switch in the first state information and the switch in the second state information matches the predetermined sequence.

10. The penile tumescence diagnosis method of claim 8, further comprising storing the sensor-sensed information detected by the plurality of ring sensors in memory based on sensing time;

wherein the generating, by the processor, diagnostic information comprises generating the diagnostic information regarding the body part based on the sensor-sensed information stored in the memory based on the sensing time.

11. The penile tumescence diagnosis method of claim 10, further comprising visualizing, by the processor, the sensor-sensed information stored in the memory based on the sensing time.

12. The penile tumescence diagnosis method of claim 11, wherein the visualizing comprises visualizing both the sensor-sensed information and a health state of the body part based on the sensing time according to information about the user.

13. The penile tumescence diagnosis method of claim 8, wherein the generating, by the processor, diagnostic information comprises:

determining whether the sensor-sensed information corresponds to a valid event based on a duration and peak value of a sensing signal included in the sensor-sensed information;

when the sensor-sensed information corresponds to a valid event, generating body information regarding the body part based on the sensor-sensed information; and when a case where the sensor-sensed information does not correspond to a valid event occurs successively, determining whether one or more of the sensors have failed, have caused error, or have been separated from the body part.

* * * * *